US005801232A

United States Patent [19]
Elliott et al.

[11] Patent Number: 5,801,232
[45] Date of Patent: Sep. 1, 1998

[54] DNA AND MRNA ENCODING HUMAN NEURONAL NICOTINIC ACETYLCHOLINE RECEPTOR ALPHA-2 SUBUNIT AND CELLS TRANSFORMED WITH SAME

[75] Inventors: Kathryn J. Elliott; Steven B. Ellis, both of San Diego; Michael M. Harpold, El Cajon, all of Calif.

[73] Assignee: SIBIA Neuroscience, Inc., La Jolla, Calif.

[21] Appl. No.: 496,855

[22] Filed: Jun. 20, 1995

Related U.S. Application Data

[63] Continuation of Ser. No. 149,503, Nov. 8, 1993, abandoned.
[51] Int. Cl.$^6$ .................................................. C12N 15/00
[52] U.S. Cl. .................. 536/23.5; 236/23.1; 435/325; 435/252.3; 435/69.1; 935/70; 935/72
[58] Field of Search ..................... 536/23.1, 23.5; 435/240.2, 252.3, 69.1, 325; 935/70, 72

[56] References Cited

U.S. PATENT DOCUMENTS

| | | |
|---|---|---|
| 4,703,008 | 10/1987 | Lin .................................. 435/240.2 |
| 4,837,148 | 6/1989 | Cregg .................................. 435/172 |
| 4,855,231 | 8/1989 | Stroman et al. ..................... 435/68 |
| 4,859,609 | 8/1989 | Dull et al. .......................... 436/501 |
| 4,882,279 | 11/1989 | Cregg ................................. 435/68 |
| 4,929,555 | 5/1990 | Cregg et al. ....................... 435/172 |
| 4,981,784 | 1/1991 | Evans et al. ......................... 435/6 |
| 5,024,939 | 6/1991 | Gorman ............................. 435/69 |
| 5,071,773 | 12/1991 | Evans et al. ....................... 436/501 |
| 5,091,518 | 2/1992 | Sucov et al. ........................ 536/27 |
| 5,369,028 | 11/1994 | Harpold et al. ................. 435/252.3 |
| 5,371,188 | 12/1994 | Heinemann et al. .............. 530/350 |
| 5,386,025 | 1/1995 | Jay et al. ............................ 536/24 |
| 5,401,629 | 3/1995 | Harpold et al. ...................... 435/6 |
| 5,436,128 | 7/1995 | Harpold et al. ...................... 435/6 |
| 5,449,606 | 9/1995 | Heinemann et al. .................. 435/6 |

FOREIGN PATENT DOCUMENTS

| | | |
|---|---|---|
| 0325849 | 8/1989 | European Pat. Off. . |
| 8803168 | 5/1988 | WIPO . |
| 8909834 | 10/1989 | WIPO . |
| 9010648 | 9/1990 | WIPO . |
| WO 90/10648 | 9/1990 | WIPO . |
| 9106677 | 5/1991 | WIPO . |
| 9115602 | 10/1991 | WIPO . |
| WO 91/15602 | 10/1991 | WIPO . |
| 9202639 | 2/1992 | WIPO . |
| 9513299 | 5/1995 | WIPO . |

OTHER PUBLICATIONS

Akong et al., Characterization of nicotinic acetylcholine receptors in human neuroblastoma cell line, *FASEB J.*, 4(3):A737 (1990).

Alam et al., Reporter genes: Application to the study of mammalian gene transcription, *Anal. Biochem.* 188:245–254 (1990).

Albuquerque et al., Neuronal nicotinic receptors: Function, modulation and structure, *Seminars in the Neurosciences* 7:91–101 (1995).

Allard et al., Sequence of the gene encoding the human M1 muscarinic acetylcholine receptor, *Nucl. Acids Res.*, 15:10604 (1987).

Alton and Vapnek, Nucleotide sequence analysis of the chloramphenicol resistance transposon Tn9, *Nature* 282:864–869 (1979).

Baldwin et al., Cloning of the luciferase structural genes from *Vibrio harveyi* and expression of bioluminescence in *Escherichia coli*, *Biochemistry* 23:3663–3667 (1984).

Ballivet et al., Electrophysiology of a chick neuronal nicotinic acetylcholine receptor expressed in *Xenopus oocytes* after cDNA injection, *Neuron* 1:847–852 (1988).

Bertrand and Changeux, Nicotinic receptor: An receptor: An allosteric protein specialized for intercellular communication, *Seminars in the Neurosciences* 7:75–90 (1995).

Blackshear et al., Protein kinase C–dependent and –independent pathways of proto–oncogene induction in human astrocytoma cells, *J. Bio. Chem.* 262(16):7774–7781 (1987).

Blanchard et al., The regulatory strategies of c–myc and c–fos proto–oncogenes share some common mechanism, *Biochimie* 70:877–884 (1988).

Bonner et al., Cloning and expression of the human and rat m5 muscarinic acetylcholine receptor genes, *Neuron* 1:403–410 (1988).

Bonnieu et al., Requirements for c–fos mRNA down regulation in growth stimulated murine cells, *Oncogene* 4:881–888 (1989).

Bouche, Basic fibroblast growth factor enters the nucleolus and stimulates the transcription of ribosomal genes in ABAE cells undergoing $G_0$–$G_1$ transition, *Proc. Natl. Acad. Sci. USA* 84:6770–6774 (1987).

Boulter et al., α3, α5, and β4: Three members of rat neuronal nicotinic acetylcholine receptor–related gene family form a gene cluster, *J. Biol. Chem.* 265:4472–4482 (1990).

Briggs et al., Human α7 nicotinic acetylcholine receptor responses to novel ligands, *Neuropharmacology* 34:583–590 (1995).

Bunzow et al., Cloning and expression of a rat $D_2$ dopamine receptor cDNA, *Nature* 336:783–787 (1988).

Changelian et al., Structure of the NGFI–A gene and detection of upstream sequences responsible for its transcriptional induction by nerve growth factor, *Proc. Natl. Acad. Sci. USA* 86:377–381 (1989).

(List continued on next page.)

*Primary Examiner*—Stephen Walsh
*Assistant Examiner*—Eliane Lazar-Wesley
*Attorney, Agent, or Firm*—Stephanie L. Seidman; Brown Martin Haller & McClain LLP

[57] ABSTRACT

DNA encoding human neuronal nicotinic acetylcholine receptor $\alpha_2$ subunits, mammalian and amphibian cells containing said DNA, and methods for producing such subunits are provided. In addition, combinations of subunits (i.e., $\alpha_2$, plus $\alpha_1$, $\alpha_3$, $\alpha_4$, and/or $\alpha_7$ subunits in combination with $\beta_2$, $\beta_3$ and/or $\beta_4$ subunits) are provided.

12 Claims, 1 Drawing Sheet

OTHER PUBLICATIONS

Chavez–Noriega et al., Characterization of recombinant human neuronal nicotinic ACh receptors expressed in HEK293 cells and Xenopus oocytes, *Soc. Neurosci. Abstr.* (1995).

Chini et al., Molecular cloning and chromosomal localization of the human $\alpha_2$-nicotinic receptor subunit gene (CHRNA7), *Genomics* 19:379–381 (1994).

Choi et al., Labeling studies of photolabile philanthotoxins with nicotinic acetylcholine receptors: Mode of interaction between toxin and receptor, *Chemistry & Biology* 2:23–32 (1995).

Cleveland et al., Number and evolutionary conservation of the $\alpha$–and $\beta$–tubulin and cytoplasmic $\beta$–and $\gamma$–actin genes using specific cloned cDNA probes, *Cell* 20:95–105 (1980).

Cohen et al., Regions of $\beta 2$ and $\beta 4$ responsible for differences between the steady state dose–response relationships of the $\alpha 3\beta 2$ and $\alpha 3\beta 4$ neuronal nicotinic receptors, *J. Gen. Physiol.* 105:745–764 (1995).

Collins et al., cAMP stimulates transcription of the $\beta_2$–adrenergic receptor gene in response to short–term agonist exposure, *Proc. Natl. Acad. Sci. USA* 86:4853–4857 (1989).

Comb et al., A cyclic AMP–and phorbol ester–inducible DNA element, *Nature* 323:353–356 (1986).

Conroy and Berg, Neurons can maintain multiple classes of nicotinic acetylcholine receptors distinguished by different subunit compositions, *J. Biol. Chem.* 270(9):4424–4431 (1995).

Cordon–Cardo et al., The trk tyrosine protein kinase mediates the mitogenic properties of nerve growth factor and neurotrophin–3, *Cell* 66:173–183 (1991).

Cotecchia et al., Multiple second messenger pathways of a $\alpha$–adrenergic receptor subtypes expressed in eukaryotic cells, *J. Biol. Chem.* 265(1):63–69 (1990).

Cross et al., Enhancement by 5–hydroxytryptamine and analogues of desensitization of neuronal and muscle nicotinic receptors expressed in Xenopus oocytes, *Br. J. Pharmacol.* 114:1636–1640 (1990).

Curran et al., Barium modulates c–fos expression and post-–translational modification, *Proc. Natl. Acad. Sci. USA* 83:8521–8524 (1986).

Curran et al., FBJ murine osterosarcoma virus: Identification and molecular cloning of biologically active proviral DNA, *J. Virology* 44(2):674–682 (1982).

Denhardt, A membrane–filter technique for the detection of complementary DNA, *Biochem. Biophys. Res. Commun.* 23:641–646 (1966).

Devreotes, *Dictyostelium discoideum*: A model system for cell–cell interactions in developments, *Science* 245:1054–1058 (1989).

deWet et al., Firefly luciferase gene: Structure and expression in mammalian cells, *Mol. Cell. Biol.* 7:725–737 (1987).

Didier et al., Characterization of nicotinic acetylcholine receptors expressed in primary cultures of cerebellar granule cells, *Mol. Brain Res.* 30:17–28 (1995).

Dixon et al., Cloning of the gene and cDNA for mammalian $\beta$–adrenergic receptor and homology with rhodopsin, *Nature* 321:75–79 (1986).

Ellis et al., Replacement of insulin receptor tyrosine residues 1162 and 1163 compromises insulin–stimulated kinase activity and uptake of 2–deoxyglucose, *Cell* 45:721–732 (1986).

Ellis et al., Sequence and expression of mRNAs encoding the $\alpha_1$ and $\alpha_2$ subunits of a DHP–sensitive calcium channel, *Science* 241:1661–1664 (1988).

Engebrecht and Silverman, Identification of genes and gene products necessary for bacterial bioluminescence, *Proc. Natl. Acad. Sci. USA* 1:4154–4158 (1984).

Fanger et al., Differential expression of sodium channels and nicotinic acetylcholine receptor channels in nnr variants of the PC12 pheochromocytoma cell line, *J. Membrane Biol.* 144:71–80 (1995).

Fink et al., The CGTCA sequence motif is essential for biological activity of the vasoactive intestinal peptide gene cAMP–regulated enhancer, *Proc. Natl. Acad. Sci. USA* 85:6662–6666 (1988).

Firtel et al., G protein linked signal transduction pathways in development: Dictyostelium as an experimental system, *Cell* 58:235–239 (1989).

Frielle et al., Cloning of the cDNA for the human $\beta_1$–adrenergic receptor, *Proc. Natl. Acad. Sci. USA* 84:7920–7924 (1987).

Galzi and Changeux, Neuronal nicotinic receptors: Molecular organization and regulations, *Neuropharmacology* 34(6):563–582 (1955).

Gautam et al., A G protein gamma subunit shares homology with ras proteins, *Science* 244:971–974 (1989).

Gilman, G proteins: Transducers of receptor–generated signals, *Ann. Rev. Biochem.* 56:615–649 (1987).

Gopalkrishnan et al., Stable expression and pharmacological properties of the human $\alpha_7$ nicotinic acetylcholine receptor, *Eur. J. Pharmacol.* 290:237–246 (1995).

Gorman et al., Recombinant genomes which express chloramphenicol acetyltransferase in mammalian cells, *Mol. Cell. Biol.* 2(9):1044–1051 (1982).

Goyal, Muscarinic receptor subtypes, *N. Eng. J. Med.* 321(15): 1022–1029 (1989).

Green berg et al., Stimulation of neuronal acetylcholine receptors induces rapid gene transcription, *Science* 234:80–83 (1986).

Groebe et al., $\alpha$–connotoxins selectively inhibit one of the two acectylcholine binding sites of the nicotinic receptors, *Mol. Pharmacol.* 48:105–111 (1995).

Hall et al., Expression and regulation of *Escherichia coli* lacZ gene fusions in mammalian cells, *J. Molec. Appl. Genet.* 2:101–109 (1983).

Hamill et al., Improved patch–clamp techniques for high–resolution current recording from cells and cell–free membrane patches, *Pflugers Arch.* 391:85–100 (1981).

Herschman, Extracellular signals, transcriptional responses and cellular specificity, *Trends Biochem. Sci.* 14:455–458 (1989).

Hollman et al., Cloning by functional expression of a member of the glutamate receptor family, *Nature* 342:643–648 (1989).

Horwitz et al., Muscarinic receptor stimulation inositol-–phospholipid metabolism and inhibits cyclic AMP accumulation in PC12 cells, *J. Neurochem.* 53:197–204 (1989).

Howard et al., Expression of nicotinic acetylcholine receptors and subunit mRNA transcripts in cultures of neural crest cells, *Dev. Biol.* 170:479–495 (1995).

Hussy et al., Agonists and antagonist effects of nicotinic on chick neuronal nicotinic receptors are defined by $\alpha$ and $\beta$ subunits, *J. Neurophysiol.* 72(3):1317–1326 (1994).

Jay et al., Primary structure of the $\gamma$ subunit of the DHP–sensitive calcium channel from skeletal muscle, *Science* 248:490–492 (1990).

Johnson et al., Expression and structure of the human NGF receptor, *Cell* 47:545–554 (1986).

Julius et al., Molecular characterization of a functional cDNA encoding the serotonin 1c receptor, *Science* 241:558–564 (1988).

Julius et al., The 5HT2 receptor defines a family of structurally distinct but functionally conserved serotonin receptors, *Proc. Natl. Acad. Sci. USA* 87:928–932 (1990).

Kayano et al., Primary structure of rat brain sodium channel III deduced from the cDNA sequence, *FEBS Lttrs.* 228:187–194 (1988).

Klein et al., A chemoattractant receptor controls development in *Dictoyostelium discoideum*, *Science* 241:1467–1472 (1988).

Kobilka et al., Cloning, sequencing, and expression of the gene coding for the human platelet $\alpha_2$-adrenergic receptor, *Science* 238:650–656 (1987).

Kobilka et al., An intronless gene encoding a potential member of the family of receptors coupled to guanine nucleotide regulatory proteins, *Nature* 329:75–79 (1987).

Lamb et al., Demonstration in living cells of an intragenic negative regulatory element within the rodent c–fos gene, *Cell*, 61:485–496 (1990).

Lambert et al., Muscarinic receptor binding characteristics of a human neuroblastomas SK–N–SH and its clones SH–SY5Y and SH–EP1, *Eur. J. Pharmacol.* 165:71–77 (1988).

Levitan et al., Structural and functional basis for GABA, receptor heterogeneity, *Nature* 335:76–79 (1988).

Listerud et al., Functional contribution of neuronal AChR subunit revealed by antisense oligonucleotides, *Science* 254:1518–1521 (1991).

Lloyd et al., SIB–1765F, a novel nicotinic agonist: Profile in models of extrapyramidal motor dysfunction, *Soc. Neurosci. Abstr.* (1995).

Lobron et al., Cellular distribution in the rat telencephalon of mRNAs encoding for the $\alpha 3$ and $\alpha 4$ subunits of the nicotinic acteylcholine receptor, *Mol. Brain Res.* 30:70–76 (1995).

London et al., In vivo labeling of nicotinic acetylcholine receptors in brain with [$^3$H]epibatidine, *Eur. J. Pharmacol.* 278:R1–R2 (1995).

Marullo et al., Expression of human $\beta 1$ and $\beta 2$ adrenergic receptors in *E. coli* as a new tool for ligand screening, *Bio/Technology* 7:923–927 (1989).

McAllister et al., Establishment of a human medulloblastoma cell line, *Int. J. Cancer* 20:206–212 (1977).

McKinnon, D., Isolation of a cDNA clone coding for a putative second potassium channel indicates the existence of a gene family, *J. Biol. Chem.* 264:8230–8236 (1989).

Mechti et al., Sequence requirements for premature transcription arrest within the first intron of the mouse c–fos gene, *Mol. Cell. Biol.* 11(5):2832–2841 (1991).

Menzaghi et al., SIB–1765F: A novel nicotinic agonist with locomotor stimulant properties in rats, *Soc. Neurosci. Abstr.* (1995).

Michel et al., PC12 phaeochromocytoma cells contain an atypical muscarinic receptor binding site, *Br. J. Pharmacol.* 97:914–920 (1989).

Monteggia et al., Cloning and transient expression of genes encoding the human $\alpha 4$ and $\beta 2$ neuronal nicotinic acetylcholine receptor (nAChR) subunits, *Gene* 155:189–193 (1995).

Montminy et al., Identification of a cyclic–AMP–responsive element within the rat somatostatin gene, *Proc. Natl. Acad. Sci. USA* 83:6682–6686 (1986).

Morgan et al., Stimulus–transcription coupling in neurons: Role of cellular immediate–early genes, *Trends Neurosci*, 12(11):459–462 (1989).

Nielsen et al., A highly sensitive, mixed–phase assay for chloramphenicol acetyltransferase activity in transfected cells, *Anal. Biochem.* 179:19–23 (1989).

Noda et al., Expression of functional sodium channels from cloned cDNA, *Nature* 322:826–828 (1986).

Noda et al., Existence of distinct sodium channel messenger RNAs in rat brain, *Nature* 320:188–192 (1986).

Nordeen, Luciferase reporter gene vectors for analysis of promoters and enhancers, *BioTechniques* 6(5):454–456 (1988).

Nutter and Adams, Monovalent and divalent cation permeability and block of neuronal nicotinic receptor channels in rat parasympathetic ganglia, *J. Gen. Physiol.* 105:701–723 (1995).

Ortells and Lunt, Evolutionary history of the ligand–gated ion–channel superfamily receptors, *Trend Neurosci.* 18(3):121–127 (1995).

Ostermann et al., Cellular expression of $\alpha 4$ subunit mRNa of the nicotinic acetylcholine receptor in the developing rat telencephalon, *Neurosci. Lttrs.* 192:21–24 (1995).

Peralta et al., Distinct primary structures, ligand–binding properties and tissue–specific expression of four hmuan muscarinic acetylcholine receptors, *EMBO J.* 6(13):3923–3929 (1987).

Peralta et al., Differential regulation of PI hydrolysis and adenylyl cyclase by mascarinic receptor subtypes, *Nature*, 334:434–437 (1988).

Picciotto et al., Abnormal avoidance learning in mice lacking functional high–affinity nicotine receptor in the brain, *Nature* 374:65–67 (1995).

Pritchett et al., Importance of a novel $GABA_A$ receptor subunit for benzodiazepine pharmacology, *Nature*, 338:582–585 (1989).

Rao et al., In vitro characterization of SIB–1765F, a novel nicotinic agonist, *Soc. Neurosci. Abstr.* (1995).

Receptor Genetics, Inc. (file of correspondence with SIBIA).

Riabowol et al., The catalytic subunit of cAMP–dependent protein kinase induces expression of genes containing cAMP–responsive enhancer elements, *Nature* 336:83–86 (1988).

Ruth et al., Primary structure of the $\beta$ subunit of the DHP–sensitive calcium channel from skeletal muscle, *Science*, 245:1115–1118 (1989).

Sacaan et al., Effect of ($\pm$)–epibatidine on the release of catecholamines: Biochemical and behavioral evidence in rats, *Soc. Neurosci. Abstr.* (1995).

Sambrook et al., *Molecular Cloning. A Laboratory Manual*, 2d Ed., Cold Spring Harbor Laboratory Press (1989).

Sargent, The diversity of neuronal nicotinic acetylcholine receptors, *Annu. Rev. Neurosci.* 16:403–443 (1993).

Sassone–Corsi et al., Induction of proto–oncogene fos transcription through the adenylate cyclase pathway: characterization of a cAMP–responsive element, *Genes Dev.* 2:1529–1538 (1988).

Schilling et al., Regulation of a fos–lacZ fusion gene: A paradigm for quantitative analysis of stimulus–transcription coupling, *Proc. Natl. Acad. Sci. USA* 88:5665–5669 (1991).

Schoepfer et al., *Molecular Biology of Neuroreceptors and Ion Channels Macelicke*, A. (Ed.), NATO–ASI Series, Springer Vergal, Heidelberg (1989).

Schofield et al., Sequence and functional expression of the $GABA_A$ receptor shows a ligand–gated receptor super–family, *Nature* 328:221–227 (1987).

Serra et al., The intact human neuroblastoma cell (SH–SY5Y) exhibits high–affinity [$^3$H]pirenzepine binding associated with hydrolysis of a phosphatidylinositols, *J. Neurochem.* 50:1513–1521 (1988).

Serra et al., Phorbol esters alter muscarinic receptor binding and inhibit polyphosphoinositide breakdown in human neuroblastoma (SH–SY5Y) cells, *Biochem. Biophys. Res. Comm.* 140:160–166 (1988).

Sheng et al., The regulation and function of c–fos and other immediate early genes in the nervous system, *Neuron* 4:477–485 (1990).

Shivers, Two novel GABA$_A$ receptor subunits exist in distinct neuronal subpopulations, *Neuron* 3:327–337 (1989).

Short et al., Characterization of the phosphoenolpyruvate carboxykinase (GTP) promoter–regulatory region, *J. Biol. Chem.* 261:9721–9726 (1986).

Stauderman et al., Characterization of recombinant human retroviral nicotinic acetylcholine receptor subtypes α4β4 and α2β4 stably expressed in HEK293 cells, *Soc. Neurosci. Abstr.* (1995).

Stillman et al., Replication and supercooling of simian virus 40 DNA in cell extracts from human cells, *Mol. Cell. Biol.* 5:2051–2060 (1985).

Stormann et al., Molecular cloning and expression of a dopamine D2 receptor from human retina, *Molec. Pharm.* 37:1–6 (1990).

Strader et al., Structural basis of β–adrenergic receptor function, *FASEB J.* 3:1825–1832 (1989).

Stumpo et al., Induction of c–fos sequences involved in induction by insulin and phorbol esters, *J. Biol. Chem.* 263(4):1611–1614 (1988).

Tanabe et al., Primary structure of the receptor for calcium channel blockers from skeletal muscle, *Nature* 328:313–318 (1987).

Tempel et al., Cloning of a probable potassium channel gene from mouse brain, *Nature* 332:837–839 (1988).

Toh et al., Isolation and characterization of a rat liver alkaline phosphatase gene, *Eur. J. Biochem.* 182:231–238 (1989).

Turchi et al., Effects of nicotinic acetylcholine receptors ligands on behavioral vigilance in rats, *Psychopharmacology* 118:195–205 (1995).

Urlaub et al., Effect of gamma rays at the dihydrofolate reductase locus: Deletions and inversions, *Somatic Cell. Molec. Genet.* 12(6):555–566 (1986).

Verna et al., Proto–oncogene fos: Complex but versatile regulation, *Cell* 51:513–514 (1987).

Visvader et al., Two adjacent promotor elements mediate nerve growth factor activation of the c–fos gene and bind distinct nuclear complexes, *Proc. Natl. Acad. Sci. USA* 85:9474–9478 (1988).

Wackym et al., Expression of α4 and β2 nicotinic acetylcholine receptor subunit mRNA and localization of α–bungarotoxin binding proteins in the rat vestibular periphery, *Cell Biology International* 19(4):291–300 (1995).

Wigler et al., DNA–mediated transfer of the adenine phosphoribosyltransferase locus into mammalian cells, *Proc. Natl. Acad. Sci. USA* 76:1373–1376 (1979).

Williams et al., Neuronal nicotinic actylcholine receptors, *Drug News & Perspectives* 7(4):205–223 (1995).

Willoughby et al., Molecular cloning of a human neuronal acetylcholine receptor β3–like subunit, *Neurosci. Lttrs.* 155:136–139 (1993).

Wilson et al., Inhibitory action of nicotinic antagonists on transmitter release at the neuromuscular junction of the rat, *Neurosci. Lttrs.* 186:29–32 (1995).

Yeh et al., Ultrastructural localization of platelet–derived growth factor/ v–sis–related protein(s) in cytoplasm and nucleus of simian sarcoma virus–transformed cells, *Proc. Natl. Acad. Sci. USA* 84:2317–2321 (1987).

Ymer et al., GABA$_A$ receptor β subunit hetrogeneity: functional expression of cloned cDNAs, *EMBO J.* 8:1665–1670 (1989).

Young et al., Isolation and charaterization of a new cellular oncogene encoding a protein with multiple potential transmembrane domains, *Cell* 45:711–719 (1986).

Zipser et al., Mapping functional domains in the promoter region of the herpes thymidine kinase gene, *Proc. Natl. Acad. Sci. USA* 78(10):6276–6280 (1981).

Anand and Lindstrom, "Nucleotide sequence of the human nicotinic acetylcholoine receptor β2 subunit gene" *Nucleic Acids Research* 18(14):4272 (1990).

Anand et al., "Neuronal Nicotinic Acetylcholline Receptors Expressed in *Xenopus Oocytes* Have a Pentameric Quaternary Structure" *Journal of Biol. Chem.* 266(17):11192–11198 (1991).

Beeson et al., "The human muscle nicotinic acetylcholine receptor α–subunit exists as two isoforms: a novel exon" *EMBO Journal* 9(7):2101–2106 (1990).

Bertrand et al., "Unconventional pharmacology of a neuronal nicotinic receptor mutated in the channel domain" *Proc. Natl. Acad. Sci. USA* 89:1261–1265 (1992).

Boulter et al., "Isolation of a cDNA clone coding for a possible neural nicotinic acetylcholine receptor α–subunit" *Nature* 319:368–374 (1986).

Boulter et al., "Functional expression of two neuronal nicotinic acetylcholine receptors from cDNA clones identifies a gene family" *Proc. Natl. Acad. Sci. USA* 84:7763–7767 (1987).

Chini et al., "Neuronal–type α–bungarotoxin receptors and the α$_5$–nicotinic receptor subunit gene are expressed in neuronal and nonneuronal human cell lines" *Proc. Natl. Acad. Sci USA* 89:1572–1576 (1992).

Clarke, Paul B.S., "The fall and rise of neuronal α–bungarotoxin binding proteins" *TIPS* 13:407–413 (1992).

Claudio et al., "Genetic Reconstitution of Functional Acetylcholine Receptor Channels in Mouse Fibroblasts" *Science* 238:1688–1694 (1987).

Clementi et al., "Pharmacological Characterization of Cholinergic Receptors in a Human Neuroblastoma Cell Line" *Journal of Neurochem.* 47(1):291–297 (1986).

Conroy et al., "The α5 Gene Product Assembles with Multiple Acetylcholine Receptor Subunits to Form Distinctive Receptor Subtypes in Brain" *Neuron* 9:679–691 (1992).

Conti–Tronconi et al., "Brain and muscle nicotinic acetylcholine receptors are different but homologous proteins" *Proc. Natl. Acad. Sci. USA* 82:5208–5121 (1985).

Cooper et al., "Pentameric structure and subunit stoichiometry of a neuronal nicotinic acetylcholine receptor" *Nature* 350:235–238 (1991).

Couturier et al., A Neuronal Nicotinic Acetylcholine Receptor Subunit (α7) Is Developmentally Regulated and Forms a Homo–Oligomeric Channel Blocked by α–BTX *Neuron* 5:847–856 (1990).

Dascal, Nathan, "The Use of *Xenopus Oocytes* for the Study of Ion Channels" *CRC Critical Reviews in Biochemistry* 22(4):317–387 (1987).

Deneris et al., "Primary Structure and Expression of β2: A Novel Subunit of Neuronal Nicotinic Acetylcholine Receptors" *Neuron* 1:45–54 (1988).

Deneris et al., "β3: A New Member of Nicotinic Acetylcholine Receptor Gene Family Is Express in Brain" *Journal of Biol. Chem.* 264(11):6268–6272 (1989).

Deneris et al., "Pharmacological and functional diversity of neuronal nicotinic acetylcholine receptors" *TIPS* 12:34–40 (1991).

Deschamps et al., "Identification of a Transcriptional Enhancer Element Upstream from the Proto–Oncogene fos" *Science* 230:1174–1177 (1985).

Doolittle, Russell F., "Of Urfs and Orfs—A Primer on How to Analyze Derived Amino Acid Sequences" University Science Books (1986).

Duvoisin et al., "The Functional Diversity of the Neuronal Nicotinic Acetylcholine Receptors Is Increased by a Novel Subunit: β4" *Neuron* 3:487–496 (1989).

Figl et al., "Regions of β4·β2 subunit chimeras that contribute to the agonist selectivity of neuronal nicotinic receptors" *FEBS* 308(3):245–248 (1992).

Fornasari et al., "Molecular cloning of human neuronal nictotinic receptor $\alpha_3$–subunit" *Neuroscience Letters* 111:351–356 (1990).

Galzi et al., "Mutations in the channel domain of a neuronal nicotinic receptor convert ion selectivity from cationic to anionic" *Nature* 359:500–505 (1992).

Goldman et al., "Members of a Nicotinic Acetylcholine Receptor Gene Family Are Expressed in Different Regions of the Mammalian Central Nervous System" *Cell* 48:965–973 (1987).

Gotti et al., "Acetylcholine Operated Ion Channel And α–Bungarotoxin Binding Site In A Human Neuroblastoma Cell Line Reside On Different Molecules" *Biochemical and Biophysical Research Communications* 137(3):1141–1147 (1986).

Halvorsen and Berg, "Affinity Labeling of Neuronal Acetylcholine Receptor Subunits with an α–Neurotoxin That Blocks Receptor Function" *Journal of Neuroscience* 7(8):2547–2555 (1987).

Ishikawa et al., "Acetylcholine Receptors of Human Skeletal Muscle: a Species Difference Detected by Snake Neurotoxins" *Brain Research* 346:82–88 (1985).

Kurosaki et al., "Functional properties of nicotinic acetylcholine receptor subunits expressed in various combinations" *FEB* 214(2):253–258 (1987).

Larsson et al., "In vitro Binding of $^3$H–Acetylcholine of Nicotinic Receptors in Rodent and Human Brain" *J. Neural Transmission* 69:3–18 (1987).

Lathe, R., "Synthetic Oligonucleotide Probes Deduced from Amino Acid Sequence Data" *J. Mol. Biol.* 183:1–12 (1985).

Luetje and Patrick, "Both α–and β–subunits Contribute to the Agonist Sensitivity of Neuronal Nicotinic Acetylcholine Receptors" *J. of Neuroscience* 11(3):837–845 (1991).

Lukas, Ronald J., "Pharmacological Distinctions between Functional Nicotinic Acetylcholine Receptors on the PC12 Rat Pheochromocytoma and the TE671 Human Medulloblastoma" *J. of Pharmacology and Experimental Therapeutics* 251(1):175–182 (1989).

Lukas et al., "Characterization of Nicotinic Acetylcholine Receptors Expressed by Cells of the SH–SY5Y Human Neuroblastoma Clonal Line" *Molec. Cell Neuroscience* 4(1):1–12 (1993).

Marshall et al., "Sequence and functional expression of a single α subunit of an insect nicotinic acetylcholine receptor" *EMBO J.* 9(13):4391–4398 (1990).

Matter–Sadzinski et al., "Neuronal specificity of the α7 nicotinic acetylcholine receptor promoter develops during morphogenesis of the cental nervous system" *EMBO Journal* 11(12):4529–4538 (1992).

Mauron et al., "Structure of Chicken Genes Encoding the Nicotinic Acetylcholine Receptor Subunits and Their Variants" *Society for Neuroscience Abstracts* vol. 17 (1991).

Nef et al., "Genes expressed in the brain define three distinct neuronal nicotinic acetylcholine receptors" *EMBO J.* 7(3):595–601 (1988).

Papke and Heinemann, "The Role of the $\beta_4$–Subunit in Determining the Kinetic Properties of Rat Neuronal Nicotinic Acetylcholine $\alpha_3$–Receptors" *J. of Physiology* 440:95–112 (1991).

Patrick et al., "Acetylcholine Receptor Metabolism in a Nonfusing Muscle Cell Line" *J. of Biol. Chem.* 252(6):2143–2153 (1977).

Quik and Geertsen, "Neuronal nicotinic α–bungarotoxin sites" *Can. J. Physiol. Pharmacol.* 66:971–979 (1988).

Revah et al., "Mutations in the channel domain alter desensitization of a neuronal nicotinic receptor" *Nature* 353:846–849 (1991).

Schoepfer et al., "The human medulloblastoma cell line TE671 expresses a muscle–like acetylcholine receptor" *FEB* 226(2):235–240 (1988).

Schoepfer et al., "cDNA Clones coding for the Structural Subunit of a Chicken Brain Nicotinic Acetylcholine Receptor" *Neuron* 1:241–248 (1988).

Schoepfer et al., "Brain α–Bungarotoxin Binding Protein cDNAs and MAbs Reveal Subtypes of This Branch of the Ligand–Gated Ion Channel Gene Superfamily" *Neuron* 5:35–48 (1990).

Stroud et al., "Nicotinic Acetylcholine Receptor Superfamily of Ligand–Gated Ion Channels" *Biochemistry* 29(50):11009–11023 (1990).

Subramani et al., "Expressed of the Mouse Dihydrofolate Reductase Complementary Deoxyribonucleic Acid in Simian Virus 40 Vectors" *Molecular and Cellular Biology* 1(9):854–864 (1981).

Sugaya et al., "Nicotinic Acetylcholine Receptor Subtypes in Human Frontal Cortex: Changes in Alzheimer's Disease" *J. of Neuroscience Research* 27:349–359 (1990).

Talib et al., "Differential expression of human nicotinic acetylcholine receptor α subunit variants in muscle and non–muscle tissues" *Nucleic Acids Research* 21(2):233–237 (1993).

Vernallis et al., "ACHR Gene Products in Chick Ciliary Ganglia: Transcripts, Subunits, and Receptor Subtypes" *Society for Neuroscience Abstracts* vol. 17 (1991).

Vijayaraghavan et al., "Nicotinic Receptors That Bind α–Bungarotoxin on Neurons Raise Intracellular Free $Ca^{2+}$" *Neuron* 8:353–362 (1992).

Wada et al., "Functional Expression of a New Pharmacological Subtype of Brain Nicotinic Acetylcholine Receptor" *Science* 240:330–334 (1988).

Wada et al., "Distribution of Alpha2, Alpha3, Alpha4, and Beta2 Neuronal Nicotinic Receptor Subunit mRNAs in the Central Nervous System: A Hybridization Histochemical Study in the Rat" *J. of Comparative Neurology* 284:314–335 (1989).

Whiting et al., "Structurally Different Neuronal Nicotinic Acetylcholine Receptor Subtypes Purified and Characterized Using Monoclonal Antibodies" *J. of Neuroscience* 7(12):4005–4016 (1987).

Whiting and Lindstrom, "Purification and characterization of a nicotinic acetylcholine receptor from rat brain" *Proc. Natl. Acad. Sci. USA* 84:595–599 (1987).

Whiting and Lindstrom, "Affinity labelling of neuronal acetylcholine receptors localizes acetylcholine–binding sites to their β–subunits" *FEB* 213(1):55–60 (1987).

Whiting et al., "Neuronal nicotinic acetylcholine receptor β–subunit is coded for by the cDNA clone $\alpha_4$" *FEB* 219(2):459–463 (1987).

Whiting et al., "Expression of nicotinic acetylcholine receptor subtypes in brain and retina" *Molecular Brain Research* 10:61–70 (1991).

Whiting et al., "Structural and Pharmacological Characterization of the Major Brain Nicotinic Acetylcholine Receptor Subtype Stably Expressed in Mouse Fibroblasts" *Molecular Pharmacology* 40:463–472 (1991).

Williams et al., Structure and functional expression of $\alpha_1$, $\alpha_2$, and β subunits of a novel human neuronal calcium channel subtypes, *Neuron* 8:71–84 (1992) Jan.

Tanabe, et al., "A Family of Metabotropic Glutamate Receptors," *Neuron*, 8:169–179 (1992).

Wood, "Gene Cloning Based on Long Oligonucleotide Probes," *Methods in Enzymology*, 152:443–447 (1987).

Doucette–Stamm et al., "Cloning and Sequence of the Human α7 Nicotinic Acetylcholine Receptor" *Drug Development Research* 30:252–256 (1993).

Elliott et al., "Cloning and Functional Expression of Human Neuronal Nicotinic Acetylcholine Receptor Subunit" *Soc. Neurosci. Abstr.* 19:69 (1993).

Nash et al., "Molecular Cloning and Expression of Human Neuronal Nicotinic Acetylcholine Receptor Subunits" *Soc. Neurosci. Abstr.* 16(1):10 (1990).

Nash et al., "Molecular Cloning of Human Neuronal Nicotinic Acetylcholine Receptor Subunits" *Feb. Am. Soc. Exp. Biol.* 4(7):A2153 (1990).

Peng et al., "Human α7 Acetylcholine Receptor: Cloning of the α7 Subunit from the SH–SY5Y Cell Line and Determination of Pharmacological Properties of Native Receptors and Functional α7 Homomers Expressed in Xenopus Oocytes" *Molecular Pharmacology* 45:546–554 (1994).

Séguéla et al., "Molecular Cloning, Functional Properties, and Distribution of Rat Brain $\alpha_7$: A Nicotinic cation Channel Highly Permeable to Calcium" *J. of Neurosci.* 13(2):596–604 (1993).

Tarroni et al., "Neuronal–type nicotinic receptors in human neuroblastoma and small–cell lung carcinoma cell lines" *FEBS Letters* 312:66–70 (1992).

Zoli et al., "Developmental Regulation of Nicotinic ACh Receptor Subunit mRNAs in the Rat Central and Peripheral Nervous Systems", *J. of Neurosci.* 15(3):1912–1939 (1995).

Zwart et al., "Differential Modulation of α3β4 Neuronal Nicotinic Receptors Expressed in *Xenopus Oocytes* by Flufenamic Acid and Niflumic Acid" *J. of Neurosci.* 15(3):2168–2178 (1995).

Sambrook et al, *Molecular Cloning*, p. 16.3 (1989).

Nash et al., FASEB, vol. 4, pp. A2153, 1990.

DNA AND MRNA ENCODING HUMAN NEURONAL NICOTINIC ACETYLCHOLINE RECEPTOR ALPHA-2 SUBUNIT AND CELLS TRANSFORMED WITH SAME

This application is a file wrapper continuation of U.S. application Ser. No. 08/149,503, filed Nov. 8, 1993, now abandoned.

FIELD OF INVENTION

This invention relates to nucleic acids encoding human neuronal nicotinic acetylcholine receptor protein subunits, as well as the proteins themselves. In particular, nucleic acids encoding human neuronal nicotinic acetylcholine receptor alpha subunits and beta subunits, and alpha subunit proteins, beta subunit proteins, and combinations thereof are provided.

BACKGROUND OF THE INVENTION

Ligand-gated ion channels provide a means for communication between cells of the central nervous system. These channels convert a signal (e.g., a chemical referred to as a neurotransmitter) that is released by one cell into an electrical signal that propagates along a target cell membrane. A variety of neurotransmitters and neurotransmitter receptors exist in the central and peripheral nervous systems. Five families of ligand-gated receptors, including the nicotinic acetylcholine receptors (NAChRs) of neuromuscular and neuronal origins, have been identified (Stroud et al. (1990) Biochemistry 29:11009–11023). There is, however, little understanding of the manner in which the variety of receptors generates different responses to neurotransmitters or to other modulating ligands in different regions of the nervous system.

The nicotinic acetylcholine receptors (NAChRs) are multisubunit proteins of neuromuscular and neuronal origins. These receptors form ligand-gated ion channels that mediate synaptic transmission between nerve and muscle and between neurons upon interaction with the neurotransmitter acetylcholine (ACh). Since various nicotinic acetylcholine receptor (NAChR) subunits exist, a variety of NAChR compositions (i.e., combinations of subunits) exist. The different NAChR compositions exhibit different specificities for various ligands and are thereby pharmacologically distinguishable. Thus, the nicotinic acetylcholine receptors expressed at the vertebrate neuromuscular junction in vertebrate sympathetic ganglia and in the vertebrate central nervous system have been distinguished on the basis of the effects of various ligands that bind to different NAChR compositions. For example, the elapid α-neurotoxins that block activation of nicotinic acetylcholine receptors at the neuromuscular junction do not block activation of some neuronal nicotinic acetylcholine receptors that are expressed on several different neuron-derived cell lines.

Muscle NAChR is a glycoprotein composed of five subunits with the stoichiometry $\alpha_2\beta(\gamma$ or $\epsilon)\delta$. Each of the subunits has a mass of about 50–60 kilodaltons (kd) and is encoded by a different gene. The $\alpha_2\beta(\gamma$ or $\epsilon)\delta$ complex forms functional receptors containing two ligand binding sites and a ligand-gated transmembrane channel. Upon interaction with a cholinergic agonist, muscle nicotinic AChRs conduct sodium ions. The influx of sodium ions rapidly short-circuits the normal ionic gradient maintained across the plasma membrane, thereby depolarizing the membrane. By reducing the potential difference across the membrane, a chemical signal is transduced into an electrical signal that signals muscle contraction at the neuromuscular junction.

Functional muscle nicotinic acetylcholine receptors have been formed with $\alpha\beta\delta\gamma$ subunits, $\alpha\beta\gamma$ subunits, $\alpha\beta\delta$ subunits, $\alpha\delta\gamma$ subunits or $\alpha\delta$ subunits, but not with only one subunit (see e.g., Kurosaki et al. (1987) FEBS Lett. 214: 253–258; Camacho et al. (1993) J. Neuroscience 13:605–613). In contrast, functional neuronal AChRs (nAChRs) can be formed from a subunits alone or combinations of α and β subunits. The larger α subunit is generally believed to be the ACh-binding subunit and the lower molecular weight β subunit is generally believed to be the structural subunit, although it has not been definitively demonstrated that the β subunit does not have the ability to bind ACh. Each of the subunits which participate in the formation of a functional ion channel are, to the extent they contribute to the structure of the resulting channel, "structural" subunits, regardless of their ability (or inability) to bind ACh. Neuronal AChRs (nAChRs), which are also ligand-gated ion channels, are expressed in ganglia of the autonomic nervous system and in the central nervous system (where they mediate signal transmission), in post-synaptic locations (where they modulate transmission), and in pre- and extra-synaptic locations (where they may have additional functions).

DNA encoding NAChRs has been isolated from several sources. Based on the information available from such work, it has been evident for some time that NAChRs expressed in muscle, in autonomic ganglia, and in the central nervous system are functionally diverse. This functional diversity could be due, at least in part, to the large number of different NAChR subunits which exist. There is an incomplete understanding, however, of how (and which) NAChR subunits combine to generate unique NAChR subtypes, particularly in neuronal cells. Indeed, there is evidence that only certain NAChR subtypes may be involved in diseases such as Alzheimer's disease. Moreover, it is not clear whether NAChRs from analogous tissues or cell types are similar across species.

Accordingly, there is a need for the isolation and characterization of nucleic acids encoding each human neuronal NAChR subunit, recombinant cells containing such subunits and receptors prepared therefrom. In order to study the function of human neuronal AChRs and to obtain disease-specific pharmacologically active agents, there is also a need to obtain isolated (preferably purified) human neuronal nicotinic AChRs, and isolated (preferably purified) human neuronal nicotinic AChR subunits. In addition, there is also a need to develop assays to identify such pharmacologically active agents.

The availability of such nucleic acids, cells, receptor subunits and receptor compositions will eliminate the uncertainty of speculating as to human nNAChR structure and function based on predictions drawn from non-human nNAChR data, or human or non-human muscle or ganglia NAChR data.

Therefore, it is an object herein to isolate and characterize nucleic acids encoding subunits of human neuronal nicotinic acetylcholine receptors. It is also an object herein to provide methods for recombinant production of human neuronal nicotinic acetylcholine receptor subunits. It is also an object herein to provide purified receptor subunits and to provide methods for screening compounds to identify compounds that modulate the activity of human neuronal AChRs.

These and other objects will become apparent to those of skill in the art upon further study of the specification and claims.

BRIEF DESCRIPTION OF THE INVENTION

In accordance with the present invention, there are provided isolated nucleic acids encoding novel human alpha subunits of neuronal NAChRs. In particular, isolated DNA encoding human $\alpha_2$ subunits of neuronal NAChRs are provided. Messenger RNA and polypeptides encoded by the above-described nucleic acids are also provided.

Further in accordance with the present invention, there are provided recombinant $\alpha_2$ subunits of human neuronal nicotinic AChRs, as well as methods for the production thereof. In addition, recombinant neuronal nicotinic acetylcholine receptors containing a human $\alpha_2$ subunit of neuronal nicotinic AChRs are also provided, as well as methods for the production thereof. Further provided are recombinant neuronal nicotinic AChRs that contain a mixture of one or more NAChR subunits encoded by a host cell, and one or more nNAChR subunits encoded by heterologous DNA or RNA (i.e., DNA or RNA as described herein that has been introduced into the host cell), as well as methods for the production thereof.

Plasmids containing DNA encoding the above-described subunits are also provided. Recombinant cells containing the above-described DNA, mRNA or plasmids are also provided herein. Such cells are useful, for example, for replicating DNA, for producing human NAChR subunits and recombinant receptors, and for producing cells that express receptors containing one or more human subunits.

Also provided in accordance with the present invention are methods for identifying cells that express functional nicotinic acetylcholine receptors. Methods for identifying compounds which modulate the activity of NAChRs are also provided.

The DNA, mRNA, vectors, receptor subunits, receptor subunit combinations and cells provided herein permit production of selected neuronal nicotinic AChR subunits and specific combinations thereof, as well as antibodies to said receptor subunits. This provides a means to prepare synthetic or recombinant receptors and receptor subunits that are substantially free of contamination from many other receptor proteins whose presence can interfere with analysis of a single NAChR subtype. The availability of desired receptor subtypes makes it possible to observe the effect of a drug substance on a particular receptor subtype and to thereby perform initial in vitro screening of the drug substance in a test system that is specific for humans and specific for a human neuronal nicotinic AChR subtype.

The availability of subunit-specific antibodies makes possible the application of the technique of immunohistochemistry to monitor the distribution and expression density of various subunits (e.g., in normal vs diseased brain tissue). Such antibodies could also be employed for diagnostic and therapeutic applications.

The ability to screen drug substances in vitro to determine the effect of the drug on specific receptor compositions should permit the development and screening of receptor subtype-specific or disease-specific drugs.

Also, testing of single receptor subunits or specific receptor subunit combinations with a variety of potential agonists or antagonists provides additional information with respect to the function and activity of the individual subunits and should lead to the identification and design of compounds that are capable of very specific interaction with one or more of the receptor subunits or receptor subtypes. The resulting drugs should exhibit fewer unwanted side effects than drugs identified by screening with cells that express a variety of subtypes.

Further in relation to drug development and therapeutic treatment of various disease states, the availability of nucleic acids encoding human nNAChR subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

DETAILED DESCRIPTION OF THE INVENTION

Figure 1A:
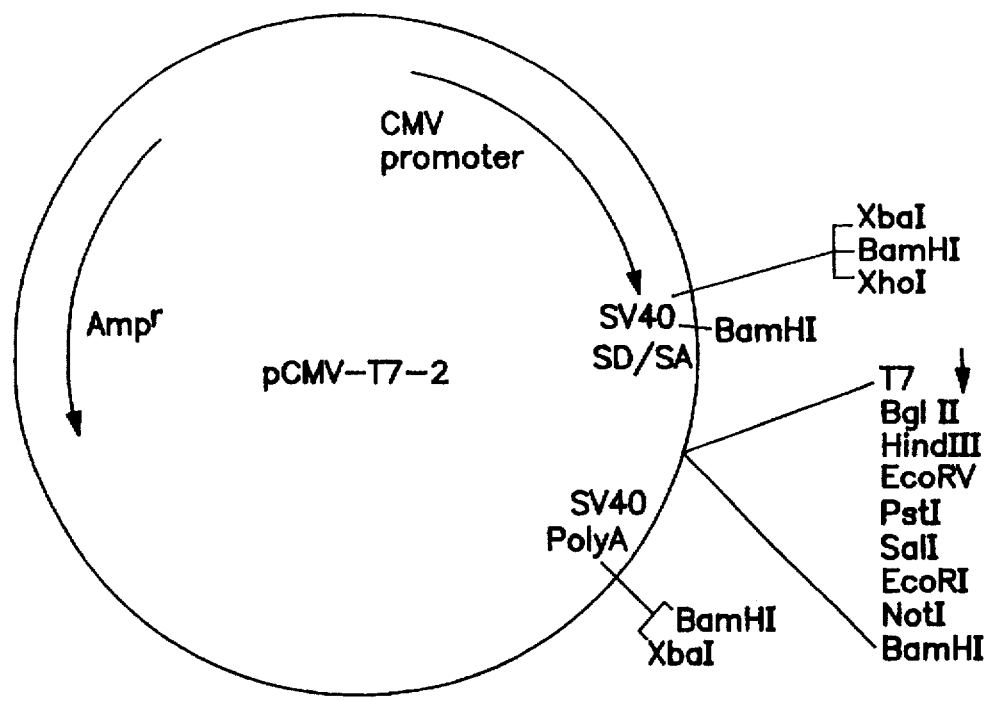
FIG. 1 presents a restriction map of two pCMV promoter-based vectors, pCMV-T7-2 and pCMV-T7-3.

In accordance with the present invention, we have isolated and characterized nucleic acids encoding a novel human alpha subunit of neuronal NAChRs. Specifically, isolated DNAs encoding a human $\alpha_2$ subunit of neuronal NAChRs are described herein. Recombinant messenger RNA (mRNA) and recombinant polypeptides encoded by the above-described nucleic acids are also provided.

As used herein, isolated (or substantially pure) as a modifier of DNA, RNA, polypeptides or proteins means that the DNA, RNA, polypeptides or proteins so designated have been separated from their in vivo cellular environments through the efforts of human beings. Thus as used herein, isolated (or substantially pure) DNA refers to DNAs purified according to standard techniques employed by those skilled in the art (see, e.g., Maniatis et al.(1982) *Molecular Cloning: A Laboratory Manual,* Cold Spring Harbor Laboratory Press, Cold Spring Harbor, N.Y.).

Similarly, as used herein, "recombinant" as a modifier of DNA, RNA, polypeptides or proteins means that the DNA, RNA, polypeptides or proteins so designated have been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

As used herein, a human alpha subunit gene is a gene that encodes an alpha subunit of a human neuronal nicotinic acetylcholine receptor. The alpha subunit is a subunit of the NAChR to which ACh binds. Assignment of the name "alpha" to a putative nNAChR subunit, according to Deneris et al. [Tips (1991) 12:34–40], is based on the conservation of adjacent cysteine residues in the presumed extracellular domain of the subunit that are the homologues of cysteines 192 and 193 of the Torpedo alpha subunit (see Noda et al. (1982) Nature 299:793–797). As used herein, an alpha subunit refers to a human nNAChR subunit that is encoded by DNA that hybridizes under high stringency conditions to the nNAChR alpha subunit-encoding DNAs disclosed herein. An alpha subunit also binds to ACh under physiological conditions and at physiological concentrations and, in the optional presence of a beta subunit (i.e., some alpha subunits are functional alone, while others require the presence of a beta subunit), generally forms a functional AChR as assessed by methods described herein or known to those of skill in this art.

As used herein, "$\alpha_2$ subunit DNA" refers to DNA encoding a neuronal nicotinic acetylcholine receptor subunit of the same name. Such DNA can be characterized in a number of ways, for example, the nucleotides of said DNA may encode the amino acid sequence set forth in SEQ. ID No. 2. Presently preferred $\alpha_2$-encoding DNAs can be characterized as DNA which hybridizes under high stringency conditions to the coding sequence set forth in SEQ. ID No. 1 (preferably to substantially the entire coding sequence thereof, i.e., nucleotides 166–1755). Especially preferred $\alpha_2$-encoding DNAs of the invention are characterized as having substantially the same nucleotide sequence as the coding region set forth in SEQ. ID No. 1 (i.e., nucleotides 166–1755 thereof).

Typically, unless an $\alpha_2$ subunit arises as a splice variant, $\alpha_2$-encoding DNA will share substantial sequence homology (i.e., greater than about 90%), with the $\alpha_2$ DNAs described herein. DNA or RNA encoding a splice variant may share less than 90% overall sequence homology with the DNA or RNA provided herein, but such a splice variant would include regions of nearly 100% homology to the above-described DNAs.

Also contemplated are alpha subunits encoded by DNAs that encode alpha subunits as defined above, but that by virtue of degeneracy of the genetic code do not necessarily hybridize to the disclosed DNA or deposited clones under specified hybridization conditions. Such subunits also contribute to the formation of a functional receptor, as assessed by the methods described herein or known to those of skill in the art, generally with one or more beta subunits. Typically, unless an alpha subunit is encoded by RNA that arises from alternative splicing (i.e., a splice variant), alpha-encoding DNA and the alpha subunit encoded thereby share substantial sequence homology with the alpha subunit DNAs (and proteins encoded thereby) described herein. It is understood that DNA or RNA encoding a splice variant may overall share less than 90% homology with the DNA or RNA provided herein, but include regions of nearly 100% homology to a DNA fragment described herein, and encode an open reading frame that includes start and stop codons and encodes a functional alpha subunit.

As used herein, a splice variant refers to variant NAChR subunit-encoding nucleic acid(s) produced by differential processing of primary transcript(s) of genomic DNA, resulting in the production of more than one type of mRNA. cDNA derived from differentially processed genomic DNA will encode NAChR subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10}[Na^+])+0.41(\% \ G+C)-600/l,$$

where l is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhardt's solution, 5× SSPE, 0.2% SDS at 42° C., followed by washing in 0.1× SSPE, and 0.1% SDS at 65° C.;

(2) MODERATE STRINGENCY refers to conditions equivalent to hybridization in 50% formamide, 5× Denhardt's solution, 5× SSPE, 0.2% SDS at 42° C., followed by washing in 0.2× SSPE, 0.2% SDS, at 65° C.; and (3) LOW STRINGENCY refers to conditions equivalent to hybridization in 10% formamide, 5× Denhardt's solution, 6× SSPE, 0.2% SDS, followed by washing in 1× SSPE, 0.2% SDS, at 50° C.

It is understood that these conditions may be duplicated using a variety of buffers and temperatures and that they are not necessarily precise.

Denhardt's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of NaH$_2$PO$_4$ and 7.4 g EDTA in 800 ml of water, adjusting the pH to 7.4, and then adding water to 1 liter. Denhardt's solution (see, Denhardt (1966) Biochem. Biophys. Res. Commun. 23:641) can be prepared, for example, as a 50× stock solution by mixing 5 g Ficoll (Type 400, Pharmacia LKB Biotechnology, INC., Piscataway N.J.), 5 g of polyvinylpyrrolidone, 5 g bovine serum albumin (Fraction V; Sigma, St. Louis Mo.) water to 500 ml and filtering to remove particulate matter.

The phrase "substantial sequence homology" is used herein in reference to the nucleotide sequence of DNA, the ribonucleotide sequence of RNA, or the amino acid sequence of protein, that have slight and non-consequential sequence variations from the actual sequences disclosed herein. Species having substantial sequence homology are considered to be equivalent to the disclosed sequences and as such are within the scope of the appended claims. In this regard, "slight and non-consequential sequence variations" mean that "homologous" sequences, i.e., sequences that have substantial homology with the DNA, RNA, or proteins disclosed and claimed herein, are functionally equivalent to the sequences disclosed and claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

In practice, the term substantially the same sequence means that DNA or RNA encoding two proteins hybridize under conditions of high stringency and encode proteins that have the same sequence of amino acids or have changes in sequence that do not alter their structure or function. As used herein, substantially identical sequences of nucleotides share at least about 90% identity, and substantially identical amino acid sequences share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

DNA encoding human neuronal nicotinic AChR $\alpha_2$ subunits may be isolated by screening suitable human cDNA or human genomic libraries under suitable hybridization conditions with DNA disclosed herein. Suitable libraries can be prepared from neuronal tissue samples, hippocampus tissue, or cell lines, such as the human neuroblastoma cell line IMR32 (ATCC Accession No. CCL127), and the like. The library is preferably screened with a portion of DNA including the entire subunit-encoding sequence thereof, or the library may be screened with a suitable probe.

As used herein, a probe is single-stranded DNA or RNA that has a sequence of nucleotides that includes at least 14 contiguous bases that are the same as (or the complement of) any 14 bases set forth in SEQ ID No. 1. Preferred regions from which to construct probes include 5' and/or 3' coding sequences, sequences predicted to encode transmembrane domains, sequences predicted to encode the cytoplasmic loop, signal sequences, acetylcholine (ACh) and $\alpha$-bungarotoxin ($\alpha$-bgtx) binding sites, and the like. Amino acids 210–220 are typically involved in ACh and $\alpha$-bgtx binding. The approximate amino acid residues which comprise such regions specifically for 2 subunits include amino acids 1–55 for the signal sequence, amino acids 264–289 for the first transmembrane domain (TMD1), amino acids 297–320 for the second transmembrane domain (TMD2), amino acids 326–350 for the third transmembrane domain (TMD3), amino acids 444–515 for the fourth transmembrane domain (TMD4), and amino acids 351–443 for the cytoplasmic loop. Alternatively, portions of the DNA can be used as primers to amplify selected fragments in a particular library.

After screening the library, positive clones are identified by detecting a hybridization signal; the identified clones are characterized by restriction enzyme mapping and/or DNA sequence analysis, and then examined, by comparison with the sequences set forth herein, to ascertain whether they include DNA encoding a complete alpha subunit. If the selected clones are incomplete, they may be used to rescreen the same or a different library to obtain overlapping clones. If desired, the library can be rescreened with positive clones until overlapping clones that encode an entire alpha subunit are obtained. If the library is a cDNA library, then the overlapping clones will include an open reading frame. If the library is genomic, then the overlapping clones may include exons and introns. In both instances, complete clones may be identified by comparison with the DNA and encoded proteins provided herein.

Complementary DNA clones encoding human nNAChR $\alpha_2$ subunits have been isolated. The DNA clones provided herein may be used to isolate genomic clones encoding such subunits and to isolate any splice variants by screening libraries prepared from different neural tissues. Nucleic acid amplification techniques, which are well known in the art, can be used to locate splice variants of human NAChR subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human NAChR subunits.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the level of skill of the art.

An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention AChR subunits in eukaryotic host cells, particularly mammalian cells, include cytomegalovirus (CMV) promoter-containing vectors such as pCMV, pcDNA1, and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove or alter 5' untranslated portions of the clones to remove extra, potential alternative translation initiation (i.e., start) codons or other sequences that interfere with or reduce expression, either at the level of transcription or translation. Alternatively, consensus ribosome binding sites (see, for example, Kozak (1991) J. Biol. Chem. 266:19867–19870) can be inserted immediately 5' of the start codon to enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCDNA1 (Invitrogen, San Diego, Calif.), and MMTV promoter-based vectors such as pMSG (Catalog No. 27-4506-01 from Pharmacia, Piscataway, N.J.).

Full-length DNAs encoding human neuronal NAChR subunits have been inserted into vector pCMV-T7, a pUC19-based mammalian cell expression vector containing the CMV promoter/enhancer, SV40 splice/donor sites located immediately downstream of the promoter, a polylinker downstream of the splice/donor sites, followed by an SV40 polyadenylation signal. Placement of NAChR subunit DNA between the CMV promoter and SV40 polyadenylation signal provides for constitutive expression of the foreign DNA in a mammalian host cell transfected with the construct. For inducible expression of human NAChR subunit-encoding DNA in a mammalian cell, the DNA can be inserted into a plasmid such as pMSG. This plasmid contains the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200). Full-length human DNA clones encoding human $\alpha_2$ subunits can also be subcloned into pIBI24 (International Biotechnologies, Inc., New Haven, Conn.) or pCMV-T7-2 for synthesis of in vitro transcripts.

In accordance with another embodiment of the present invention, there are provided cells containing the above-described polynucleic acids (i.e., DNA or mRNA). Such host cells as bacterial, yeast and mammalian cells can be used for replicating DNA and producing nAChR subunit(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/02311, PCT/US91/05625 and PCT/US92/11090, and in co-pending U.S. application Ser. Nos. 07/504,455, 07/563,751 and 07/812,254. The subject matter of these applications are hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subunit(s) encoded by the DNA is (are) expressed. Preferred cells include mammalian cells (e.g., HEK 293, CHO and Ltk⁻ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929, 555 and 4,855,231), *Saccharomyces cerevisiae*, *Candida tropicalis*, *Hansenula polymorpha*, and the like), mammalian expression systems, including commercially available systems and other such systems known to those of skill in the art, for expression of DNA encoding the human neuronal nicotinic AChR subunits provided herein are presently preferred. Xenopus oocytes are preferred for expression of RNA transcripts of the DNA.

In preferred embodiments, DNA is ligated into a vector, and introduced into suitable host cells to produce transformed cell lines that express a specific human nNAChR receptor subtype, or specific combinations of subtypes. The resulting cell lines can then be produced in quantity for reproducible quantitative analysis of the effects of drugs on receptor function. In other embodiments, mRNA may be produced by in vitro transcription of DNA encoding each subunit. This mRNA, either from a single subunit clone or from a combination of clones, can then be injected into Xenopus oocytes where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Cloned full-length DNA encoding any human neuronal nicotinic AChR subunit(s) may be introduced into a plasmid vector for expression in a eukaryotic cell. Such DNA may be genomic DNA or cDNA. Host cells may be transfected with one or a combination of plasmids, each of which encodes at least one human neuronal nicotinic AChR subunit.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human neuronal nicotinic AChRs comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney cells, African green monkey cells and other such cells known to those of skill in the art), amphibian cells (e.g., *Xenopus laevis* oocytes), yeast cells (e.g., *Saccharomyces cerevisiae*, *Pichia pastoris*), and the like. Exemplary cells for expressing injected RNA transcripts include *Xenopus laevis* oocytes. Cells that are preferred for transfection of DNA are known to those of skill in the art or may be empirically identified, and include HEK 293 (which are available from ATCC under accession #CRL 1573); Ltk⁻ cells (which are available from ATCC under accession #CCL1.3); COS-7 cells (which are available from ATCC under accession #CRL 1651); and DG44 cells (dhfr⁻ CHO cells; see, e.g., Urlaub et al. (1986) Cell. Molec. Genet. 12: 555). Presently preferred cells include DG44 cells and HEK 293 cells, particularly HEK 293 cells that have been adapted for growth in suspension and that can be frozen in liquid nitrogen and then thawed and regrown. HEK 293 cells are described, for example, in U.S. Pat. No. 5,024,939 to Gorman (see, also, Stillman et al. (1985) Mol. Cell. Biol. 5:2051–2060).

DNA may be stably incorporated into cells or may be transiently introduced using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To produce such cells, the cells should be transfected with a sufficient concentration of subunit-encoding nucleic acids to form human neuronal nicotinic AChRs that contain the human subunits encoded by heterologous DNA. The precise amounts and ratios of DNA encoding the subunits may be empirically determined and optimized for a particular combination of subunits, cells and assay conditions. Recombinant cells that express neuronal nicotinic AChR containing subunits encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human neuronal nicotinic AChR subunits may be purified using protein purification methods known to those of skill in the art. For example, antibodies or other ligands that specifically bind to one or more of the subunits may be used for affinity purification of the subunit or human neuronal nicotinic AChRs containing the subunits.

In accordance with one embodiment of the present invention, methods for producing cells that express human neuronal nicotinic AChR subunits and functional receptors are also provided. In one such method, host cells are transfected with DNA encoding an $\alpha_2$ subunit of a neuronal nicotinic acetylcholine receptor and a beta subunit of a neuronal nicotinic acetylcholine receptor. Using methods such as northern blot or slot blot analysis, transfected cells that contain alpha $\alpha_2$ and, optionally, beta subunit encoding DNA or RNA, can be selected. Transfected cells are also analyzed to identify those that express NAChR protein. Analysis can be carried out, for example, by measuring the ability of cells to bind acetylcholine, nicotine, or a nicotine agonist, compared to the nicotine binding ability of untransfected host cells or other suitable control cells, by electrophysiologically monitoring the currents through the cell membrane in response to a nicotine agonist, and the like.

As used herein, a human beta subunit gene is a gene that encodes a beta subunit of a human neuronal nicotinic acetylcholine receptor. Assignment of the name "beta" to a putative nNAChR subunit, according to Deneris et al. supra, is based on the lack of adjacent cysteine residues (which are characteristic of alpha subunits). The beta subunit is frequently referred to as the structural NAChR subunit (although it is possible that beta subunits also have ACh binding properties). Combination of beta subunit(s) with appropriate alpha subunit(s) leads to the formation of a functional receptor. A beta subunit forms a functional NAChR, as assessed by methods described herein or known to those of skill in this art, with appropriate alpha subunit subtype(s).

In particularly preferred aspects, eukaryotic cells which contain heterologous DNAs express such DNA and form recombinant functional neuronal nicotinic AChR(s). In more preferred aspects, recombinant neuronal nicotinic AChR activity is readily detectable because it is a type that is absent from the untransfected host cell or is of a magnitude not exhibited in the untransfected cell. Such cells that contain recombinant receptors could be prepared, for example, by causing cells transformed with DNA encoding human neuronal nicotinic AChR $\alpha_2$ and $\beta_2$ subunits to express the corresponding proteins. The resulting synthetic or recombinant receptor would contain only the $\alpha_2$ and $\beta_2$ nNAChR subunits. Such a receptor would be useful for a variety of applications, e.g., as part of an assay system free of the interferences frequently present in prior art assay systems employing non-human receptors or human tissue preparations. Furthermore, testing of single receptor subunits with a variety of potential agonists or antagonists would provide additional information with respect to the function and activity of the individual subunits. Such information is expected to lead to the identification of compounds which are capable of very specific interaction with one or more of the receptor subunits. Such specificity may prove of great value in medical application.

Thus, DNA encoding one or more human neuronal nicotinic AChR subunits may be introduced into suitable host cells (e.g., eukaryotic or prokaryotic cells) for expression of individual subunits and functional NAChRs. Preferably combinations of alpha and beta subunits may be introduced into cells: such combinations include combinations of $\alpha_2$, optionally in the further presence of any one or more of $\alpha_1$, $\alpha_3$, $\alpha_4$, $\alpha_5$ and $\alpha_7$, with $\beta_2$ or $\beta_4$.

Sequence information for al is presented in Biochem. Soc. Trans. (1989) 17:219–220; sequence information for $\alpha_2$ is presented herein; sequence information for $\alpha_3$ is presented in U.S. Ser. No. 07/504,455, filed Apr. 3, 1990, now pending; sequence information for $\alpha_4$ is presented in U.S. Ser. No. 08/028,031, filed Mar. 8, 1993, now pending; sequence information for $\alpha_5$ is presented in Proc. Natl. Acad. Sci.USA (1992) 89:1572–1576; and sequence information for $\alpha_7$ is presented in U.S. Ser. No. 08/028,031, filed Mar. 8, 1993, now pending.

Sequence information for $\beta_2$ is presented in SEQ ID NOS: 3 and 4; and sequence information for $\beta_4$ is presented in SEQ ID NOS: 5 and 6.

In certain embodiments, eukaryotic cells with heterologous human neuronal nicotinic AChRs are produced by introducing into the cell a first composition, which contains at least one RNA transcript that is translated in the cell into a subunit of a human neuronal nicotinic AChR. In preferred embodiments, the composition that is introduced contains an RNA transcript which encodes a human $\alpha_2$ subunit and also contains an RNA transcript which encodes a beta subunit of a human neuronal nicotinic AChR. RNA transcripts can be obtained from cells transfected with DNAs encoding human neuronal nicotinic acetylcholine receptor subunits or by in vitro transcription of subunit-encoding DNAs. Methods for in vitro transcription of cloned DNA and injection of the resulting mRNA into eukaryotic cells are well known in the art. Amphibian oocytes are particularly preferred for expression of in vitro transcripts of the human nNAChR DNA clones provided herein. See, for example, Dascal (1989) CRC Crit. Rev. Biochem. 22:317–387, for a review of the use of Xenopus oocytes to study ion channels.

Thus, pairwise (or stepwise) introduction of DNA or RNA encoding alpha and beta subtypes into cells is possible. The resulting cells may be tested by the methods provided herein or known to those of skill in the art to detect functional AChR activity. Such testing will allow the identification of pairs of alpha and beta subunit subtypes that produce functional AChRs, as well as individual subunits that produce functional AChRs.

As used herein, activity of a human neuronal nicotinic AChR refers to any activity characteristic of an NAChR. Such activity can typically be measured by one or more in vitro methods, and frequently corresponds to an in vivo activity of a human neuronal nicotinic AChR. Such activity may be measured by any method known to those of skill in the art, such as, for example, measuring the amount of current which flows through the recombinant channel in response to a stimulus.

Methods to determine the presence and/or activity of human neuronal nicotinic AChRs include assays that measure nicotine binding, $^{86}$Rb ion-flux, $Ca^{2+}$ influx, the electrophysiological response of cells, the electrophysiological response of oocytes transfected with RNA from the cells, and the like. In particular, methods are provided herein for the measurement or detection of an AChR-mediated response upon contact of cells containing the DNA or mRNA with a test compound.

As used herein, a recombinant or heterologous human neuronal nicotinic AChR refers to a receptor that contains one or more subunits encoded by heterologous DNA that has been introduced into and expressed in cells capable of expressing receptor protein. A recombinant human neuronal nicotinic AChR may also include subunits that are produced by DNA endogenous to the host cell. In certain embodiments, recombinant or heterologous human neuronal nicotinic AChR may contain only subunits that are encoded by heterologous DNA.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human neuronal nicotinic AChR subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human neuronal nicotinic AChR subunits, or may contain a mixture of subunits encoded by the host cell and subunits encoded by heterologous DNA or mRNA. Recombinant receptors may be homogeneous or may be a mixture of subtypes. Mixtures of DNA or mRNA encoding receptors from various species, such as rats and humans, may also be introduced into the cells. Thus, a cell can be prepared that expresses recombinant receptors containing only $\alpha_2$ and either $\beta_2$ or $\beta_4$ subunits.

As used herein, a functional neuronal nicotinic AChR is a receptor that exhibits an activity of neuronal nicotinic AChRs as assessed by any in vitro or in vivo assay disclosed herein or known to those of skill in the art. Possession of any such activity that may be assessed by any method known to those of skill in the art and provided herein is sufficient to designate a receptor as functional. Methods for detecting NAChR protein and/or activity include, for example, assays that measure nicotine binding, $^{86}$Rb ion-flux, $Ca^+$ influx, the electrophysiological response of cells containing heterologous DNA or mRNA encoding one or more receptor subunit subtypes, and the like. As used herein, "functional" with respect to a recombinant or heterologous human neuronal nicotinic AChR means that the receptor channel is able to provide for and regulate entry of human neuronal nicotinic AChR-permeable ions, such as, for example, $Na^+$, $K^+$, $Ca^{2+}$ or $Ba^{2+}$, in response to a stimulus and/or bind ligands with affinity for the receptor. Preferably such human neuronal nicotinic AChR activity is distinguishable, such as by electrophysiological, pharmacological and other means known to those of skill in the art, from any endogenous nicotinic AChR activity that may be produced by the host cell.

In accordance with a particular embodiment of the present invention, recombinant human neuronal nicotinic AChR-expressing mammalian cells or oocytes can be contacted with a test compound, and the modulating effect(s) thereof can then be evaluated by comparing the AChR-mediated response in the presence and absence of test compound, or by comparing the AChR-mediated response of test cells, or control cells (i.e., cells that do not express nNAChRs), to the presence of the compound.

As used herein, a compound or signal that "modulates the activity of a neuronal nicotinic AChR" refers to a compound or signal that alters the activity of NAChR so that activity of the NAChR is different in the presence of the compound or signal than in the absence of the compound or signal. In particular, such compounds or signals include agonists and antagonists. The term agonist refers to a substance or signal, such as ACh, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human neuronal nicotinic AChR activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express functional human neuronal nicotinic AChRs. In this situation, the response of test cell to test compound is compared to the response (or lack of response) of receptor-negative (control) cell to test compound, when cells or cultures of each type of cell are exposed to substantially the same reaction conditions in the presence of compound being assayed.

Functional recombinant human neuronal nicotinic AChRs contemplated by the present invention include at least an $\alpha_2$ subunit, or an $\alpha_2$ subunit and a beta subunit of a human neuronal nicotinic AChR. Eukaryotic cells expressing these subunits have been prepared by injection of RNA transcripts and by transfection of DNA. Such cells have exhibited nicotinic AChR activity attributable to human neuronal nicotinic AChRs that contain one or more of the heterologous human neuronal nicotinic AChR subunits.

With respect to measurement of the activity of functional heterologous human neuronal nicotinic AChRs, endogenous AChR activity and, if desired, activity of AChRs that contain a mixture of endogenous host cell subunits and heterologous subunits, should, if possible, be inhibited to a significant extent by chemical, pharmacological and electrophysiological means.

The invention will now be described in greater detail with reference to the following non-limiting examples.

EXAMPLE 1

Isolation of DNA Encoding Human nNAChR $\alpha_2$ Subunits

RNA isolated from human thalamus tissue was used in synthesizing cDNA for λgt11-based cDNA library. The library constructed from the cDNAs was screened for hybridization to a fragment of a rat nicotinic AChR $\alpha_2$ subunit cDNA, using low stringency wash conditions.

Hybridizing clones were plaque-purified and characterized by restriction enzyme mapping and DNA sequence analysis. The insert DNA of one of the clones contained a translation initiation codon and nearly the complete coding sequence of an $\alpha_2$ subunit of a human nicotinic AChR, except for ~77 bp at the 3' end. This insert was ligated with the insert of another clone containing the complete 3' end of the $\alpha_2$ subunit coding sequence to generate a full-length $\alpha_2$ subunit cDNA. The full-length cDNA was isolated and ligated into the polylinker of vector pIBI24 to generate h$\alpha$2/pIBI24.

To verify the $\alpha$2 subunit coding sequence in h$\alpha$2/pIBI24 near nucleotide 450, human thalamus cDNAs were subjected to nucleic acid amplification using oligonucleotides SE153 and SE154 as primers. These oligonucleotides correspond to human $\alpha$2 subunit-coding sequence located 5' and 3' of nucleotide 450. SE153, corresponding to the extreme 5' end of the $\alpha$2 subunit-coding sequence, also contained nucleotides corresponding to a consensus ribosome binding site (RBS). Consequently, the product of the amplification contained an RBS (GCCACC) immediately 5' of the translation initiation codon.

The expected ~660-bp product was obtained from the amplification reaction. The product was digested with EcoRI/SstI and an ~560-bp fragment, comprising the 5' end of the $\alpha$2 subunit coding sequence, was ligated with EcoRI/SstI-digested pIBI24 to create h$\alpha$2-5'/PIBI. To generate full-length $\alpha$2 subunit cDNA, a DNA fragment containing the 3' end of the $\alpha$2 subunit coding sequence was ligated to the 5' fragment contained in h$\alpha$2-5'/PIBI as follows.

Plasmid h$\alpha$2/PIBI24 was digested with ClaI, followed by partial digestion with SstI. The 1.7-kb fragment containing the 3' portion of the $\alpha$2 subunit coding sequence was isolated and ligated with SstI-digested h$\alpha$2-5'/PIBI to create PIBI-KE$\alpha$2RBS. This construct contains the correct full-length $\alpha$2 subunit coding sequence preceded immediately by an RBS.

EXAMPLE 2

Preparation of Constructs for the Expression of Recombinant Human Neuronal Nicotinic AChR $\alpha_2$ Subunits Isolated cDNAs encoding human neuronal nicotinic AChR subunits were incorporated into vectors for use in expressing the subunits in mammalian host cells and for use in generating in vitro transcripts of the DNAs to be expressed in Xenopus oocytes. Several different vectors were utilized in preparing the constructs as follows.

A. Construct for Expression of a Human nNAChR $\alpha_2$ Subunit

Figure 1B:
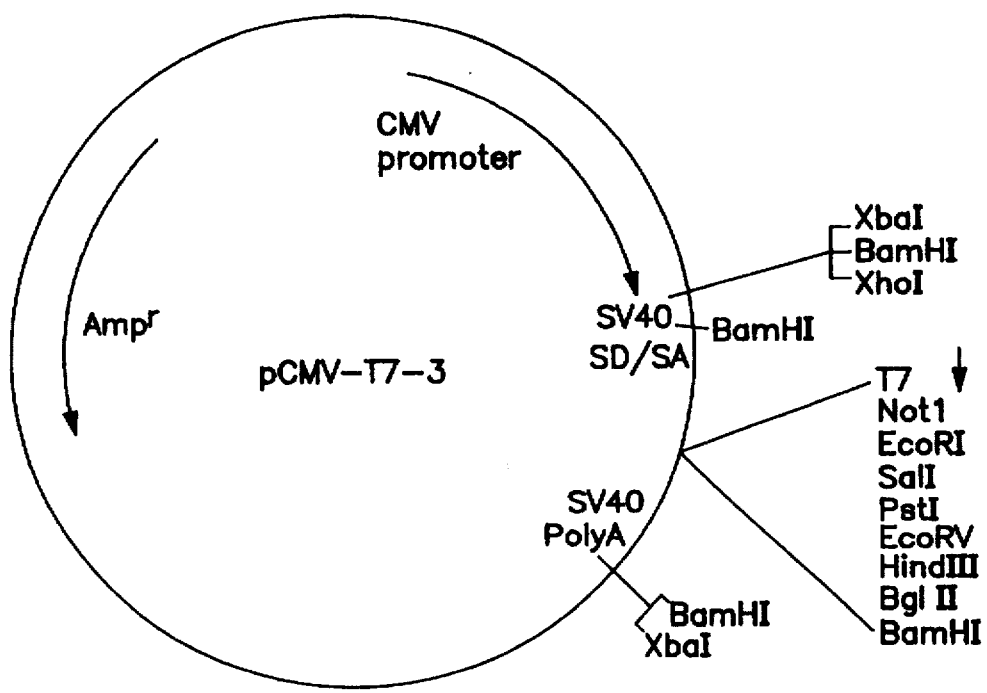

DNA encoding a human neuronal nicotinic AChR $\alpha_2$ subunit was subcloned into the pCMV-T7-3 general expression vector to create pCMV-KE$\alpha$2RBSf. Plasmid pCMV-T7-3 (see FIG. 1) is a pUC19-based vector that contains a CMV promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. FIG. 1 also shows a restriction map of pCMV-T7-2. This plasmid is identical to pCMV-T7-3 except that the restriction sites in the polylinker are in the opposite order as compared to the order in which they occur in pCMV-T7-3.

The insert in pIBI-KE$\alpha$2RBS (see Example 1) was isolated as an EcoRI fragment and ligated with EcoRI-digested pCMV-T7-3 to generate pCMV-KE$\alpha$2RBSf. Construct pCMV-KE$\alpha$2RBSf contains the $\alpha$2 subunit coding sequence preceded immediately by an RBS and followed by 316 bp of 3' untranslated sequence. The coding sequence is operably positioned downstream of the T7 promoter thereby enabling the generation of in vitro transcripts of the cDNA.

B. Construct for Expression of a Human nNAChR $\beta_2$ Subunit

DNA encoding a human NAChR $\beta$2 subunit (see U.S. patent application Ser. Nos. 07/504,455 and 08/028,031 for such DNAS) was incorporated into expression vector pSP64T. Vector pSP64T [see Krieg and Melton (1984) *Nuc. Acids Res.* 12:7057–7070] is a modified form of vector pSP64 (Promega). The human NAChR $\beta$2 subunit coding sequence (preceded by an RBS) was incorporated into pSP64T at a unique restriction enzyme cloning site that is flanked by 5' and 3' untranslated sequences from the Xenopus $\beta$-globin gene. These sequences are located downstream of the SP6 promoter contained in pSP64T. The resulting vector, pSP64T-KE$\beta$2RBS1, contains the human NAChR $\beta$2 subunit coding sequence in operable association with SP6 transcription regulatory regions for the production of in vitro transcripts of the heterologous DNA.

EXAMPLE 3

Expression of Recombinant Human Nicotinic AChR in Oocytes

Xenopus oocytes were injected with in vitro transcripts prepared from constructs containing DNA encoding $\alpha_2$ and $\beta_2$ subunits. Electrophysiological measurements of the oocyte transmembrane currents were made using the two-electrode voltage clamp technique (see, e.g., Stuhmer (1992) *Meth. Enzymol.* 207:319–339).

1. Preparation of in vitro transcripts

Recombinant capped transcripts of pCMV-KE$\alpha$2RBSf were synthesized from linearized plasmids using the mMessage mMachine T7 (Ambion Cat. #1334). Recombinant capped transcripts of pSP64T-KE$\beta$2RBS1 were synthesized from linearized plasmids using the MEGAscript SP6 in vitro transcription kit according to the capped transcript protocol provided by the manufacturer (Catalog #1330 from AMBION, Inc., Austin, Tex.). The mass of each synthesized transcript was determined by UV absorbance and the integrity of each transcript was determined by electrophoresis through an agarose gel.

2. Electrophysiology

Xenopus oocytes were injected with 10 ng of each human nicotinic AChR subunit transcript per oocyte. The preparation and injection of oocytes were carried out as described by Dascal (1987) in *Crit. Rev. Biochem.* 22:317–387. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 mM HEPES, pH 7.3) containing 1 μM atropine. Cells were voltage-clamped at −80 mV. Data were acquired with Axotape software (AXON Instruments) at ~2 Hz. The agonists acetylcholine (ACh), nicotine, 1,1-dimethyl-4-phenylpiperazinium (DMPP) and cytosine were added at a concentration of about 1 μM.

For the purpose of comparing the relative potencies of the four different agonists (i.e., nicotine, acetylcholine, cytosine and DMPP), oocytes were exposed to 1 μM doses of each agonist, and the current responses recorded. The responses were normalized to the response of 1 μM ACh (designated as 1.00 (see following table).

| $\alpha_2\beta_2$ Normalized Response | |
|---|---|
| ACh | 1.00 |
| Nicotine | 0.33 ± 0.06 |
| DMPP | 0.40 ± 0.15 |
| Cytosine | 0.09 ± 0.04 | n = 4

The recombinant oocytes exhibited detectable current responses to all four agonists. The data in the table presented above demonstrate that NAChRs expressed in oocytes injected with transcripts of human $\alpha_2$ and $\beta_2$ subunit cDNAs have the following relative sensitivities to the agonists:

ACh>DMPP≈nicotine>cytosine

EXAMPLE 4

Recombinant Expression of Human nNAChR $\alpha_2$ Subunits in Mammalian Cells

Human embryonic kidney (HEK) 293 cells or other suitable host cells can be transiently and stably transfected with DNA encoding human neuronal nicotinic AChR alpha and beta subunits. Transfectants are analyzed for expression of nicotinic AChR using various assays, e.g., electrophysiological methods, $Ca^{2+}$-sensitive fluorescent indicator-based assays and nicotine-binding assays.

A. Transient Transfection of Host Cells

In transient transfections, ~2×10⁶ host cells, e.g., HEK293 cells, are transiently transfected with 18 μg of plasmid(s) containing NAChR subunit DNAs according to standard $CaPO_4$ transfection procedures [Wigler et al. (1979) *Proc. Natl. Acad. Sci. USA* 76:1373–1376]. In addition, 2 μg of plasmid pCMVβgal (Clontech Laboratories, Palo Alto, Calif.), which contains the *Escherichia coli* β-galactosidase gene fused to the CMV promoter, are co-transfected as a reporter gene for monitoring the efficiency of transfection. The transfectants are analyzed for β-galactosidase expression by measurement of β-galactosidase activity [Miller (1972) Experiments in Molecular Genetics, pp.352–355, Cold Spring Harbor Press]. Transfectants can also be analyzed for β-galactosidase expression by direct staining of the product of a reaction involving β-galactosidase and the X-gal substrate [Jones (1986) *EMBO* 5:3133–3142].

B. Stable Transfection of Host Cells

For stable transfection, host cells, such as HEK 293 cells, can be transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million host cells are transfected with 1 ml of DNA/calcium phosphate precipitate containing ~19 μg total of NAChR α and β subunit construct DNA, and 1 μg selectable marker DNA, e.g., pSV2neo. Typically, after 14 days of growth in selection media containing, for example, 1 μg/ml G418, colonies form and are individually isolated by using cloning cylinders. The isolates are subjected to limiting dilution and screened to identify those that express the highest level of nicotinic AChR, as described below.

EXAMPLE 5

Characterization of Cell Lines Expressing nNAChRs

Recombinant cell lines generated by transfection with DNA encoding human neuronal nicotinic AChRs, such as those described in Example 3, can be further characterized using one or more of the following methods.

A. Fluorescent indicator-based assays

Activation of the ligand-gated nicotinic AChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying nicotinic AChR has been described in commonly assigned pending U.S. patent application Ser. No. 07/812,254 and corresponding PCT Patent Application No. US92/11090.

Host cells that are transiently or stably co-transfected with DNA encoding alpha and beta subunits can be analyzed for expression of functional recombinant nicotinic AChR using the automated fluorescent indicator-based assay. The assay procedure is as follows.

Untransfected host cells and host cells that have been transfected with DNA encoding alpha and beta subunits are plated in the wells of a 96-well microtiter dish and loaded with fluo-3 by incubation for 2 hours at 20° C. in a medium containing 20 μM fluo-3, 0.2% Pluronic F-127 in HBS (125 mM NaCl, 5 mM KCl, 1.8 mM CaCl$_2$, 0.62 mM MgSO$_4$, 6 mM glucose, 20 mM HEPES, pH 7.4). The cells are then washed with assay buffer (i.e., HBS). The antagonist d-tubocurarine can be added to some of the wells at a final concentration of 10 µM. The microtiter dish is then placed into a fluorescence plate reader and the basal fluorescence of each well is measured and recorded before addition of 200 µM nicotine to the wells. The fluorescence of the wells is monitored repeatedly during a period of approximately 60 seconds following addition of nicotine.

B. Northern or slot blot analysis for expression of α- and/or β-subunit encoding messages Total RNA is isolated from ~1×10$^7$ cells and 10–15 µg of RNA from each cell type is used for northern or slot blot hybridization analysis. The inserts from human neuronal NAChR-encoding plasmids can be nick-translated and used as probe. In addition, the β-actin gene sequence (Cleveland et al. (1980) Cell 20:95–105) can be nick-translated and used as a control probe on duplicate filters to confirm the presence or absence of RNA on each blot and to provide a rough standard for use in quantitating differences in α- or β-specific mRNA levels between cell lines. Typical northern and slot blot hybridization and wash conditions are as follows:

hybridization in 5× SSPE, 5× Denhardt's solution, 50% formamide, at 42° C. followed by washing in 0.2× SSPE, 0.1% SDS, at 65° C.

C. Nicotine-binding assay

Cell lines generated by transfection with human neuronal nicotinic AChR α- or α- and β-subunit-encoding DNA can be analyzed for their ability to bind nicotine, for example, as compared to control cell lines: neuronally-derived cell lines PC12 (Boulter et al., (1986), supra; ATCC #CRL1721) and IMR32 (Clementi, et al. (1986); Int. J. Neurochem. 47:291–297; ATCC #CCL127), and muscle-derived cell line BC3H1 (Patrick, et al., (1977); J. Biol. Chem. 252:2143–2153). Negative control cells (i.e., host cells from which the transfectants were prepared) are also included in the assay. The assay is conducted as follows:

Just prior to being assayed, transfected cells are removed from plates by scraping. Positive control cells used are PC12, BC3H1, and IMR32 (which had been starved for fresh media for seven days). Control cell lines are removed by rinsing in 37° C. assay buffer (50 mM Tris/HCl, 1 mM MgCl$_2$, 2 mM CaCl$_2$, 120 mM NaCl, 3 mM EDTA, 2 mg/ml BSA and 0.1% aprotinin at pH7.4). The cells are washed and resuspended to a concentration of 1×10$^6$/250 µl. To each plastic assay tube is added 250 µl of the cell solution, 15 nM $^3$H-nicotine, with or without 1 mM unlabeled nicotine, and assay buffer to make a final volume of 500 µl. The assays for the transfected cell lines are incubated for 30 min at room temperature; the assays of the positive control cells are incubated for 2 min at 1° C. After the appropriate incubation time, 450 µl aliquots of assay volume are filtered through Whatman GF/C glass fiber filters which has been pretreated by incubation in 0.05% polyethyleneimine for 24 hours at 4° C. The filters are then washed twice, with 4 ml each wash, with ice cold assay buffer. After washing, the filters are dried, added to vials containing 5 ml scintillation fluid and radioactivity is measured.

D. $^{86}$Rb ion-flux assay

The ability of nicotine or nicotine agonists and antagonists to mediate the influx of $^{86}$Rb into transfected and control cells has been found to provide an indication of the presence of functional AChRs on the cell surface. The $^{86}$Rb ion-flux assay is conducted as follows:

1. The night before the experiment, cells are plated at 2×10$^6$ per well (i.e., 2 ml per well) in a 6-well polylysine-coated plate.

2. The culture medium is decanted and the plate washed with 2 ml of assay buffer (50 mM HEPES, 260 mM sucrose, 5.4 mM KCl, 1.8 mM CaCl$_2$, 0.8 mM MgSo$_4$, 5.5. mM glucose) at room temperature.

3. The assay buffer is decanted and 1 ml of assay buffer, containing 3 µCi/ml $^{86}$Rb, with 5 mM ouabain and agonist or antagonist in a concentration to effect a maximum response, is added.

4. The plate is incubated on ice at 1° C. for 4 min.

5. The buffer is decanted into a waste container and each well was washed with 3 ml of assay buffer, followed by two washes of 2 ml each.

6. The cells are lysed with 2×0.5 ml of 0.2% SDS per well and transferred to a scintillation vial containing 5 ml of scintillation fluid.

7. The radioactivity contained in each vial is measured and the data calculated.

Positive control cells provided the following data in this assay:

|  | PC12 | | IMR32 | |
| --- | --- | --- | --- | --- |
|  | EC$_{50}$ | Maximum response | EC$_{50}$ | Maximum response |
| Agonist | | | | |
| nicotine | 52 µM | 2.1X* | 18 µM | 7.7X* |
| CCh* | 35 µM | 3.3X$^b$ | 230 µM | 7.6X$^c$ |
| cytisine | 57 µM | 3.6X$^d$ | 14 µM | 10X* |
| Antagonist | | | | |
| d-tubocurarine | 0.81 µM | | 2.5 µM | |
| mecamylamine | 0.42 µM | | 0.11 µM | |
| hexamethonium | nd$^f$ | | 22 µM | |
| atropine | 12.5 µM | | 43 µM | |

*CCh = carbamylcholine
*200 µM nicotine
$^b$300 µM CCh
$^c$3 mM CCh
$^d$1 mM cytisine
*100 µM cytisine
$^f$nd = not determined E. Electrophysiological Analysis of Mammalian Cells Transfected with Human Neuronal Nicotinic AChR Subunit-encoding DNA Electrophysiological measurements may be used to assess the activity of recombinant receptors or to assess the ability of a test compound to potentiate, antagonize or otherwise modulate the magnitude and duration of the flow of cations through the ligand-gated recombinant AChR. The function of the expressed neuronal AChR can be assessed by a variety of electrophysiological techniques, including two-electrode voltage clamp and patch clamp methods. The cation-conducting channel intrinsic to the AChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques. In preferred embodiments, transfected mammalian cells or injected oocytes are analyzed electrophysiologically for the presence of AChR agonist-dependent currents.

While the invention has been described in detail with reference to certain preferred embodiments thereof, it will be understood that modifications and variations are within the spirit and scope of that which is described and claimed.

That which is claimed:

1. An isolated nucleic acid, comprising a sequence of nucleotides encoding an α2 subunit of a human neuronal nicotinic acetylcholine receptor, wherein the sequence of nucleotides encodes an amino acid sequence having more than 95% identity with the amino acid sequence set forth in SEQ. ID No.2.

2. An isolated nucleic acid, comprising a sequence of nucleotides encoding an α2 subunit of a human neuronal nicotinic acetylcholine receptor, wherein the sequence of nucleotides hybridizes under conditions of high stringency with the complement of nucleotides 166–1755 set forth in SEQ. ID No.1 or shares at least about 90% identity to nucleotides 166–1755 in SEQ ID No:1.

3. Recombinant cells, comprising a nucleic acid of claim 1.

4. The cells of claim 3, wherein said that are selected from bacterial cells or eukaryotic cells.

5. The cell of claim 3, wherein: the cell is an amphibian oöcyte or a mammalian cell and;
   the cell comprises a functional neuronal nicotinic acetylcholine receptor that contains one or more subunits encoded by said nucleic acid.

6. The nucleic acid of claim 1 that is mRNA.

7. A recombinant cell, comprising the mRNA of claim 6.

8. Recombinant eukaryotic cells, comprising a nucleic acid of claim 2.

9. The nucleic acid of claim 2 that is mRNA.

10. A recombinant cell, comprising the mRNA of claim 9.

11. The nucleic acid of claim 1, wherein the sequence of nucleotides encodes the sequence of amino acids set forth in SEQ ID No. 2.

12. The nucleic acid of claim 2, wherein the sequence of nucleotides is nucleotides 166–1755 of SEQ ID No. 1.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2277 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 166..1755

( x i ) SEQUENCE DESCRIPTION: SEQ ID NO:1:

```
CAATGACCTG TTTTCTTCTG TAACCACAGG TTCGGTGGTG AGAGGAACCT TCGCAGAATC        60

CAGCAGAATC CTCACAGAAT CCAGCAGCAG CTCTGCTGGG ACATGGTCC ATGGTGCAAC       120

CCACAGCAAA GCCCTGACCT GACCTCCTGA TGCTCAGGAG AAGCC ATG GGC CCC          174
                                                  Met Gly Pro
                                                   1

TCC TGT CCT GTG TTC CTG TCC TTC ACA AAG CTC AGC CTG TGG TGG CTC        222
Ser Cys Pro Val Phe Leu Ser Phe Thr Lys Leu Ser Leu Trp Trp Leu
      5                  10                  15

CTT CTG ACC CCA GCA GGT GGA GAG GAA GCT AAG CGC CCA CCT CCC AGG        270
Leu Leu Thr Pro Ala Gly Gly Glu Glu Ala Lys Arg Pro Pro Pro Arg
 20                  25                  30                  35

GCT CCT GGA GAC CCA CTC TCC TCT CCC AGT CCC ACG GCA TTG CCG CAG        318
Ala Pro Gly Asp Pro Leu Ser Ser Pro Ser Pro Thr Ala Leu Pro Gln
             40                  45                  50

GGA GGC TCG CAT ACC GAG ACT GAG GAC CGG CTC TTC AAA CAC CTC TTC        366
Gly Gly Ser His Thr Glu Thr Glu Asp Arg Leu Phe Lys His Leu Phe
                 55                  60                  65

CGG GGC TAC AAC CGC TGG GCG CGC CCG GTG CCC AAC ACT TCA GAC GTG        414
Arg Gly Tyr Asn Arg Trp Ala Arg Pro Val Pro Asn Thr Ser Asp Val
         70                  75                  80

GTG ATT GTG CGC TTT GGA CTG TCC ATC GCT CAG CTC ATC GAT GTG GAT        462
Val Ile Val Arg Phe Gly Leu Ser Ile Ala Gln Leu Ile Asp Val Asp
     85                  90                  95

GAG AAG AAC CAA ATG ATG ACC ACC AAC GTC TGG CTA AAA CAG GAG TGG        510
Glu Lys Asn Gln Met Met Thr Thr Asn Val Trp Leu Lys Gln Glu Trp
100                 105                 110                 115

AGC GAC TAC AAA CTG CGC TGG AAC CCC GCT GAT TTT GGC AAC ATC ACA        558
Ser Asp Tyr Lys Leu Arg Trp Asn Pro Ala Asp Phe Gly Asn Ile Thr
                120                 125                 130

TCT CTC AGG GTC CCT TCT GAG ATG ATC TGG ATC CCC GAC ATT GTT CTC        606
Ser Leu Arg Val Pro Ser Glu Met Ile Trp Ile Pro Asp Ile Val Leu
            135                 140                 145

TAC AAC AAT GCA GAT GGG GAG TTT GCA GTG ACC CAC ATG ACC AAG GCC        654
Tyr Asn Asn Ala Asp Gly Glu Phe Ala Val Thr His Met Thr Lys Ala
        150                 155                 160

CAC CTC TTC TCC ACG GGC ACT GTG CAC TGG GTG CCC CCG GCC ATC TAC        702
His Leu Phe Ser Thr Gly Thr Val His Trp Val Pro Pro Ala Ile Tyr
    165                 170                 175

AAG AGC TCC TGC AGC ATC GAC GTC ACC TTC TTC CCC TTC GAC CAG CAG        750
Lys Ser Ser Cys Ser Ile Asp Val Thr Phe Phe Pro Phe Asp Gln Gln
180                 185                 190                 195
```

-continued

| | | | | | | | | | | | | | | | |
|---|---|---|---|---|---|---|---|---|---|---|---|---|---|---|---|
| AAC | TGC | AAG | ATG | AAG | TTT | GGC | TCC | TGG | ACT | TAT | GAC | AAG | GCC | AAG | ATC | 798 |
| Asn | Cys | Lys | Met 200 | Lys | Phe | Gly | Ser | Trp 205 | Thr | Tyr | Asp | Lys | Ala 210 | Lys | Ile | |
| GAC | CTG | GAG | CAG | ATG | GAG | CAG | ACT | GTG | GAC | CTG | AAG | GAC | TAC | TGG | GAG | 846 |
| Asp | Leu | Glu | Gln 215 | Met | Glu | Gln | Thr | Val 220 | Asp | Leu | Lys | Asp | Tyr 225 | Trp | Glu | |
| AGC | GGC | GAG | TGG | GCC | ATC | GTC | AAT | GCC | ACG | GGC | ACC | TAC | AAC | AGC | AAG | 894 |
| Ser | Gly | Glu 230 | Trp | Ala | Ile | Val | Asn 235 | Ala | Thr | Gly | Thr | Tyr 240 | Asn | Ser | Lys | |
| AAG | TAC | GAC | TGC | TGC | GCC | GAG | ATC | TAC | CCC | GAC | GTC | ACC | TAC | GCC | TTC | 942 |
| Lys | Tyr 245 | Asp | Cys | Cys | Ala | Glu 250 | Ile | Tyr | Pro | Asp | Val 255 | Thr | Tyr | Ala | Phe | |
| GTC | ATC | CGG | CGG | CTG | CCG | CTC | TTC | TAC | ACC | ATC | AAC | CTC | ATC | ATC | CCC | 990 |
| Val 260 | Ile | Arg | Arg | Leu | Pro 265 | Leu | Phe | Tyr | Thr | Ile 270 | Asn | Leu | Ile | Ile | Pro 275 | |
| TGC | CTG | CTC | ATC | TCC | TGC | CTC | ACT | GTG | CTG | GTC | TTC | TAC | CTG | CCC | TCC | 1038 |
| Cys | Leu | Leu | Ile | Ser 280 | Cys | Leu | Thr | Val | Leu 285 | Val | Phe | Tyr | Leu | Pro 290 | Ser | |
| GAC | TGC | GGC | GAG | AAG | ATC | ACG | CTG | TGC | ATT | TCG | GTG | CTG | CTG | TCA | CTC | 1086 |
| Asp | Cys | Gly | Glu 295 | Lys | Ile | Thr | Leu | Cys 300 | Ile | Ser | Val | Leu | Leu 305 | Ser | Leu | |
| ACC | GTC | TTC | CTG | CTC | CTC | ATC | ACT | GAG | ATC | ATC | CCG | TCC | ACC | TCG | CTG | 1134 |
| Thr | Val | Phe 310 | Leu | Leu | Leu | Ile | Thr 315 | Glu | Ile | Ile | Pro | Ser 320 | Thr | Ser | Leu | |
| GTC | ATC | CCG | CTC | ATC | GGC | GAG | TAC | CTG | CTG | TTC | ACC | ATG | ATC | TTC | GTC | 1182 |
| Val | Ile 325 | Pro | Leu | Ile | Gly | Glu 330 | Tyr | Leu | Leu | Phe | Thr 335 | Met | Ile | Phe | Val | |
| ACC | CTG | TCC | ATC | GTC | ATC | ACC | GTC | TTC | GTG | CTC | AAT | GTG | CAC | CAC | CGC | 1230 |
| Thr | Leu | Ser | Ile | Val 340 | Ile | Thr | Val | Phe | Val 345 | Leu | Asn | Val | His | His 350 | Arg 355 | |
| TCC | CCC | AGC | ACC | CAC | ACC | ATG | CCC | CAC | TGG | GTG | CGG | GGG | GCC | CTT | CTG | 1278 |
| Ser | Pro | Ser | Thr | His 360 | Thr | Met | Pro | His | Trp 365 | Val | Arg | Gly | Ala | Leu 370 | Leu | |
| GGC | TGT | GTG | CCC | CGG | TGG | CTT | CTG | ATG | AAC | CGG | CCC | CCA | CCA | CCC | GTG | 1326 |
| Gly | Cys | Val | Pro 375 | Arg | Trp | Leu | Leu | Met 380 | Asn | Arg | Pro | Pro | Pro 385 | Pro | Val | |
| GAG | CTC | TGC | CAC | CCC | CTA | CGC | CTG | AAG | CTC | AGC | CCC | TCT | TAT | CAC | TGG | 1374 |
| Glu | Leu | Cys | His 390 | Pro | Leu | Arg | Leu | Lys 395 | Leu | Ser | Pro | Ser 400 | Tyr | His | Trp | |
| CTG | GAG | AGC | AAC | GTG | GAT | GCC | GAG | GAG | AGG | GAG | GTG | GTG | GTG | GAG | GAG | 1422 |
| Leu | Glu | Ser | Asn | Val 405 | Asp | Ala | Glu | Glu | Arg 410 | Glu | Val | Val | Val 415 | Glu | Glu | |
| GAG | GAC | AGA | TGG | GCA | TGT | GCA | GGT | CAT | GTG | GCC | CCC | TCT | GTG | GGC | ACC | 1470 |
| Glu | Asp | Arg | Trp | Ala 420 | Cys | Ala | Gly | His | Val 425 | Ala | Pro | Ser | Val | Gly 430 | Thr 435 | |
| CTC | TGC | AGC | CAC | GGC | CAC | CTG | CAC | TCT | GGG | GCC | TCA | GGT | CCC | AAG | GCT | 1518 |
| Leu | Cys | Ser | His | Gly 440 | His | Leu | His | Ser | Gly 445 | Ala | Ser | Gly | Pro | Lys 450 | Ala | |
| GAG | GCT | CTG | CTG | CAG | GAG | GGT | GAG | CTG | CTG | CTA | TCA | CCC | CAC | ATG | CAG | 1566 |
| Glu | Ala | Leu | Leu 455 | Gln | Glu | Gly | Glu | Leu 460 | Leu | Leu | Ser | Pro | His 465 | Met | Gln | |
| AAG | GCA | CTG | GAA | GGT | GTG | CAC | TAC | ATT | GCC | GAC | CAC | CTG | CGG | TCT | GAG | 1614 |
| Lys | Ala | Leu | Glu 470 | Gly | Val | His | Tyr | Ile 475 | Ala | Asp | His | Leu | Arg 480 | Ser | Glu | |
| GAT | GCT | GAC | TCT | TCG | GTG | AAG | GAG | GAC | TGG | AAG | TAT | GTT | GCC | ATG | GTC | 1662 |
| Asp | Ala | Asp | Ser | Ser 485 | Val | Lys | Glu | Asp | Trp 490 | Lys | Tyr | Val | Ala | Met 495 | Val | |
| ATC | GAC | AGG | ATC | TTC | CTC | TGG | CTG | TTT | ATC | ATC | GTC | TGC | TTC | CTG | GGG | 1710 |
| Ile | Asp | Arg | Ile | Phe 500 | Leu | Trp | Leu | Phe | Ile 505 | Ile | Val | Cys | Phe | Leu 510 | Gly 515 | |

| ACC | ATC | GGC | CTC | TTT | CTG | CCT | CCG | TTC | CTA | GCT | GGA | ATG | ATC | TGACTGCACC | 1762 |
| Thr | Ile | Gly | Leu | Phe | Leu | Pro | Pro | Phe | Leu | Ala | Gly | Met | Ile | | |
| | | | | 520 | | | | | 525 | | | | 530 | | |

```
TCCCTCGAGC TGGCTCCCAG GGCAAGGGG AGGGTTCTTG GATGTGGAAG GGCTTTGAAC   1822
AATGTTTAGA TTTGGAGATG AGCCCAAAGT GCCAGGGAGA ACAGCCAGGT GAGGTGGGAG   1882
GTTGGAGAGC CAGGTGAGGT CTCTCTAAGT CAGGCTGGGG TTGAAGTTTG GAGTCTGTCC   1942
GAGTTTGCAG GGTGCTGAGC TGTATGGTCC AGCAGGGGAG TAATAAGGGC TCTTCCGGAA   2002
GGGGAGGAAG CGGGAGGCAG GGCCTGCACC TGATGTGGAG GTACAGGGCA GATCTTCCCT   2062
ACCGGGGAGG GATGGATGGT TGGATACAGG TGGCTGGGCT ATTCCATCCA TCTGGAAGCA   2122
CATTTGAGCC TCCAGGCTTC TCCTTGACGT CATTCCTCTC CTTCCTTGCT CCAAAATGGC   2182
TCTGCACCAG CCGGCCCCCA GGAGGTCTGG CAGAGCTGAG AGCCATGGCC TGCAGGGGCT   2242
CCATATGTCC CTACGCGTGC AGCAGGCAAA CAAGA                              2277
```

( 2 ) INFORMATION FOR SEQ ID NO:2:

( i ) SEQUENCE CHARACTERISTICS:
      ( A ) LENGTH: 529 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| Met | Gly | Pro | Ser | Cys | Pro | Val | Phe | Leu | Ser | Phe | Thr | Lys | Leu | Ser | Leu |
| 1 | | | | 5 | | | | | 10 | | | | | 15 | |
| Trp | Trp | Leu | Leu | Leu | Thr | Pro | Ala | Gly | Glu | Glu | Ala | Lys | Arg | Pro | |
| | | | 20 | | | | | 25 | | | | 30 | | | |
| Pro | Pro | Arg | Ala | Pro | Gly | Asp | Pro | Leu | Ser | Ser | Pro | Ser | Pro | Thr | Ala |
| | | 35 | | | | 40 | | | | | 45 | | | | |
| Leu | Pro | Gln | Gly | Gly | Ser | His | Thr | Glu | Thr | Glu | Asp | Arg | Leu | Phe | Lys |
| | 50 | | | | | 55 | | | | 60 | | | | | |
| His | Leu | Phe | Arg | Gly | Tyr | Asn | Arg | Trp | Ala | Arg | Pro | Val | Pro | Asn | Thr |
| 65 | | | | | 70 | | | | 75 | | | | | | 80 |
| Ser | Asp | Val | Val | Ile | Val | Arg | Phe | Gly | Leu | Ser | Ile | Ala | Gln | Leu | Ile |
| | | | | 85 | | | | | 90 | | | | | 95 | |
| Asp | Val | Asp | Glu | Lys | Asn | Gln | Met | Met | Thr | Thr | Asn | Val | Trp | Leu | Lys |
| | | | | 100 | | | | 105 | | | | | 110 | | |
| Gln | Glu | Trp | Ser | Asp | Tyr | Lys | Leu | Arg | Trp | Asn | Pro | Ala | Asp | Phe | Gly |
| | | | 115 | | | | | 120 | | | | | 125 | | |
| Asn | Ile | Thr | Ser | Leu | Arg | Val | Pro | Ser | Glu | Met | Ile | Trp | Ile | Pro | Asp |
| | 130 | | | | | 135 | | | | | 140 | | | | |
| Ile | Val | Leu | Tyr | Asn | Asn | Ala | Asp | Gly | Glu | Phe | Ala | Val | Thr | His | Met |
| 145 | | | | | 150 | | | | | 155 | | | | | 160 |
| Thr | Lys | Ala | His | Leu | Phe | Ser | Thr | Gly | Thr | Val | His | Trp | Val | Pro | Pro |
| | | | | 165 | | | | | 170 | | | | | 175 | |
| Ala | Ile | Tyr | Lys | Ser | Ser | Cys | Ser | Ile | Asp | Val | Thr | Phe | Phe | Pro | Phe |
| | | | | 180 | | | | | 185 | | | | | 190 | |
| Asp | Gln | Gln | Asn | Cys | Lys | Met | Lys | Phe | Gly | Ser | Trp | Thr | Tyr | Asp | Lys |
| | | | | 195 | | | | | 200 | | | | | 205 | |
| Ala | Lys | Ile | Asp | Leu | Glu | Gln | Met | Glu | Gln | Thr | Val | Asp | Leu | Lys | Asp |
| | | 210 | | | | | 215 | | | | | 220 | | | |
| Tyr | Trp | Glu | Ser | Gly | Glu | Trp | Ala | Ile | Val | Asn | Ala | Thr | Gly | Thr | Tyr |
| 225 | | | | | 230 | | | | | 235 | | | | | 240 |
| Asn | Ser | Lys | Lys | Tyr | Asp | Cys | Cys | Ala | Glu | Ile | Tyr | Pro | Asp | Val | Thr |

```
                            245                       250                       255
Tyr  Ala  Phe  Val  Ile  Arg  Arg  Leu  Pro  Leu  Phe  Tyr  Thr  Ile  Asn  Leu
               260                      265                     270
Ile  Ile  Pro  Cys  Leu  Leu  Ile  Ser  Cys  Leu  Thr  Val  Leu  Val  Phe  Tyr
               275                      280                     285
Leu  Pro  Ser  Asp  Cys  Gly  Glu  Lys  Ile  Thr  Leu  Cys  Ile  Ser  Val  Leu
          290                      295                     300
Leu  Ser  Leu  Thr  Val  Phe  Leu  Leu  Leu  Ile  Thr  Glu  Ile  Ile  Pro  Ser
305                      310                      315                          320
Thr  Ser  Leu  Val  Ile  Pro  Leu  Ile  Gly  Glu  Tyr  Leu  Leu  Phe  Thr  Met
               325                      330                     335
Ile  Phe  Val  Thr  Leu  Ser  Ile  Val  Ile  Thr  Val  Phe  Val  Leu  Asn  Val
               340                      345                     350
His  His  Arg  Ser  Pro  Ser  Thr  His  Thr  Met  Pro  His  Trp  Val  Arg  Gly
          355                      360                     365
Ala  Leu  Leu  Gly  Cys  Val  Pro  Arg  Trp  Leu  Leu  Met  Asn  Arg  Pro  Pro
          370                      375                     380
Pro  Pro  Val  Glu  Leu  Cys  His  Pro  Leu  Arg  Leu  Lys  Leu  Ser  Pro  Ser
385                      390                      395                          400
Tyr  His  Trp  Leu  Glu  Ser  Asn  Val  Asp  Ala  Glu  Glu  Arg  Glu  Val  Val
                    405                      410                     415
Val  Glu  Glu  Glu  Asp  Arg  Trp  Ala  Cys  Ala  Gly  His  Val  Ala  Pro  Ser
               420                      425                     430
Val  Gly  Thr  Leu  Cys  Ser  His  Gly  His  Leu  His  Ser  Gly  Ala  Ser  Gly
               435                      440                     445
Pro  Lys  Ala  Glu  Ala  Leu  Leu  Gln  Glu  Gly  Glu  Leu  Leu  Leu  Ser  Pro
          450                      455                     460
His  Met  Gln  Lys  Ala  Leu  Glu  Gly  Val  His  Tyr  Ile  Ala  Asp  His  Leu
465                      470                      475                          480
Arg  Ser  Glu  Asp  Ala  Asp  Ser  Ser  Val  Lys  Glu  Asp  Trp  Lys  Tyr  Val
                    485                      490                     495
Ala  Met  Val  Ile  Asp  Arg  Ile  Phe  Leu  Trp  Leu  Phe  Ile  Ile  Val  Cys
               500                      505                     510
Phe  Leu  Gly  Thr  Ile  Gly  Leu  Phe  Leu  Pro  Pro  Phe  Leu  Ala  Gly  Met
          515                      520                     525
Ile
```

( 2 ) INFORMATION FOR SEQ ID NO:3:

( i ) SEQUENCE CHARACTERISTICS:
        ( A ) LENGTH: 1521 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: misc_feature
        ( B ) LOCATION: 1..1521
        ( D ) OTHER INFORMATION: /note= "Human neuronal NAChR beta-2
        cDNA shown as top nucleotide sequence in
        Figure..."

( x i ) SEQUENCE DESCRIPTION: SEQ ID NO:3:

```
ATGCCCGCTG  GCATGGCCCG  GCGCTGCGGC  CCCGTGGCGC  TGCTCCTTGG  CTTCGGCCTC    60
CTCCGGCTGT  GCTCAGGGGT  GTGGGGTACG  GATACAGAGG  AGCGGCTGGT  GGAGCATCTC   120
CTGGATCCTT  CCCGCTACAA  CAAGCTTATC  CGCCCAGCCA  CCAATGGCTC  TGAGCTGGTG   180
```

```
ACAGTACAGC TTATGGTGTC ACTGGCCCAG CTCATCAGTG TGCATGAGCG GGAGCAGATC      240

ATGACCACCA ATGTCTGGCT GACCCAGGAG TGGGAAGATT ATCGCCTCAC CTGGAAGCCT      300

GAAGAGTTTG ACAACATGAA GAAAGTTCGG CTCCCTTCCA AACACATCTG GCTCCAGAT      360

GTGGTCCTGT ACAACAATGC TGACGGCATG TACGAGGTGT CCTTCTATTC CAATGCCGTG      420

GTCTCCTATG ATGGCAGCAT CTTCTGGCTG CCGCCTGCCA TCTACAAGAG CGCATGCAAG      480

ATTGAAGTAA AGCACTTCCC ATTTGACCAG CAGAACTGCA CCATGAAGTT CCGTTCGTGG      540

ACCTACGACC GCACAGAGAT CGACTTGGTG CTGAAGAGTG AGGTGGCCAG CCTGGACGAC      600

TTCACACCTA GTGGTGAGTG GGACATCGTG GCGCTGCCGG GCCGCGGCAA CGAGAACCCC      660

GACGACTCTA CGTACGTGGA CATCACGTAT GACTTCATCA TTCGCCGCAA GCCGCTCTTC      720

TACACCATCA ACCTCATCAT CCCCTGTGTG CTCATCACCT CGCTAGCCAT CCTTGTCTTC      780

TACCTGCCAT CCGACTGTGG CGAGAAGATG ACGTTGTGCA TCTCAGTGCT GCTGGCGCTC      840

ACGGTCTTCC TGCTGCTCAT CTCCAAGATC GTGCCTCCCA CCTCCCTCGA CGTGCCGCTC      900

GTCGGCAAGT ACCTCATGTT CACCATGGTG CTTGTCACCT TCTCCATCGT CACCAGCGTG      960

TGCGTGCTCA ACGTGCACCA CCGCTCGCCC ACCACGCACA CCATGGCGCC CTGGGTGAAG     1020

GTCGTCTTCC TGGAGAAGCT GCCCGCGCTG CTCTTCATGC AGCAGCCACG CCATCATTGC     1080

GCCCGTCAGC GCCTGCGCCT GCGGCGACGC CAGCGTGAGC GCGAGGGCGC TGGAGCCCTC     1140

TTCTTCCGCG AAGCCCCAGG GGCCGACTCC TGCACGTGCT TCGTCAACCG CGCGTCGGTG     1200

CAGGGGTTGG CCGGGGCCTT CGGGGCTGAG CCTGCACCAG TGGCGGGCCC CGGGCGCTCA     1260

GGGGAGCCGT GTGGCTGTGG CCTCCGGGAG GCGGTGGACG GCGTGCGCTT CATCGCAGAC     1320

CACATGCGGA GCGAGGACGA TGACCAGAGC GTGAGTGAGG ACTGGAAGTA CGTCGCCATG     1380

GTGATCGACC GCCTCTTCCT CTGGATCTTT GTCTTTGTCT GTGTCTTTGG CACCATCGGC     1440

ATGTTCCTGC AGCCTCTCTT CCAGAACTAC ACCACCACCA CCTTCCTCCA CTCAGACCAC     1500

TCAGCCCCCA GCTCCAAGTG A                                                1521
```

(2) INFORMATION FOR SEQ ID NO:4:

(i) SEQUENCE CHARACTERISTICS:
       (A) LENGTH: 502 amino acids
       (B) TYPE: amino acid
       (D) TOPOLOGY: linear (ii) MOLECULE TYPE: protein (xi) SEQUENCE DESCRIPTION: SEQ ID NO:4:

```
Met Ala Arg Arg Cys Gly Pro Val Ala Leu Leu Leu Gly Phe Gly Leu
  1               5                  10                  15

Leu Arg Leu Cys Ser Gly Val Trp Gly Thr Asp Thr Glu Glu Arg Leu
             20                  25                  30

Val Glu His Leu Leu Asp Pro Ser Arg Tyr Asn Lys Leu Ile Arg Pro
         35                  40                  45

Ala Thr Asn Gly Ser Glu Leu Val Thr Val Gln Leu Met Val Ser Leu
     50                  55                  60

Ala Gln Leu Ile Ser Val His Glu Arg Glu Gln Ile Met Thr Thr Asn
 65                  70                  75                  80

Val Trp Leu Thr Gln Glu Trp Glu Asp Tyr Arg Leu Thr Trp Lys Pro
                 85                  90                  95

Glu Glu Phe Asp Asn Met Lys Lys Val Arg Leu Pro Ser Lys His Ile
            100                 105                 110
```

-continued

| | | | | | | | | | | | | | | |
|---|---|---|---|---|---|---|---|---|---|---|---|---|---|---|
| Trp | Leu | Pro 115 | Asp | Val | Val | Leu 120 | Tyr | Asn | Asn | Ala | Asp 125 | Gly | Met | Tyr | Glu |
| Val | Ser 130 | Phe | Tyr | Ser | Asn 135 | Ala | Val | Val | Ser | Tyr 140 | Asp | Gly | Ser | Ile | Phe |
| Trp 145 | Leu | Pro | Pro | Ala 150 | Ile | Tyr | Lys | Ser | Ala 155 | Cys | Lys | Ile | Glu | Val | Lys 160 |
| His | Phe | Pro | Phe | Asp 165 | Gln | Gln | Asn | Cys | Thr 170 | Met | Lys | Phe | Arg | Ser 175 | Trp |
| Thr | Tyr | Asp | Arg 180 | Thr | Glu | Ile | Asp | Leu 185 | Val | Leu | Lys | Ser | Glu 190 | Val | Ala |
| Ser | Leu | Asp 195 | Asp | Phe | Thr | Pro | Ser 200 | Gly | Glu | Trp | Asp | Ile 205 | Val | Ala | Leu |
| Pro | Gly 210 | Arg | Gly | Asn | Glu | Asn 215 | Pro | Asp | Asp | Ser | Thr 220 | Tyr | Val | Asp | Ile |
| Thr 225 | Tyr | Asp | Phe | Ile | Ile 230 | Arg | Arg | Lys | Pro | Leu 235 | Phe | Tyr | Thr | Ile | Asn 240 |
| Leu | Ile | Ile | Pro | Cys 245 | Val | Leu | Ile | Thr | Ser 250 | Leu | Ala | Ile | Leu | Val 255 | Phe |
| Tyr | Leu | Pro | Ser 260 | Asp | Cys | Gly | Glu | Lys 265 | Met | Thr | Leu | Cys | Ile 270 | Ser | Val |
| Leu | Leu | Ala 275 | Leu | Thr | Val | Phe | Leu 280 | Leu | Leu | Ile | Ser | Lys 285 | Ile | Val | Pro |
| Pro | Thr 290 | Ser | Leu | Asp | Val | Pro 295 | Leu | Val | Gly | Lys | Tyr 300 | Leu | Met | Phe | Thr |
| Met 305 | Val | Leu | Val | Thr | Phe 310 | Ser | Ile | Val | Thr | Ser 315 | Val | Cys | Val | Leu | Asn 320 |
| Val | His | His | Arg | Ser 325 | Pro | Thr | Thr | His | Thr 330 | Met | Ala | Pro | Trp | Val 335 | Lys |
| Val | Val | Phe | Leu 340 | Glu | Lys | Leu | Pro | Ala 345 | Leu | Leu | Phe | Met | Gln 350 | Gln | Pro |
| Arg | His | His 355 | Cys | Ala | Arg | Gln | Arg 360 | Leu | Arg | Leu | Arg | Arg 365 | Arg | Gln | Arg |
| Glu | Arg 370 | Glu | Gly | Ala | Gly | Ala 375 | Leu | Phe | Phe | Arg | Glu 380 | Ala | Pro | Gly | Ala |
| Asp 385 | Ser | Cys | Thr | Cys | Phe 390 | Val | Asn | Arg | Ala | Ser 395 | Val | Gln | Gly | Leu | Ala 400 |
| Gly | Ala | Phe | Gly | Ala 405 | Glu | Pro | Ala | Pro | Val 410 | Ala | Gly | Pro | Gly | Arg 415 | Ser |
| Gly | Glu | Pro | Cys 420 | Gly | Cys | Gly | Leu | Arg 425 | Glu | Ala | Val | Asp | Gly 430 | Val | Arg |
| Phe | Ile | Ala 435 | Asp | His | Met | Arg | Ser 440 | Glu | Asp | Asp | Asp | Gln 445 | Ser | Val | Ser |
| Glu | Asp 450 | Trp | Lys | Tyr | Val | Ala 455 | Met | Val | Ile | Asp | Arg 460 | Leu | Phe | Leu | Trp |
| Ile 465 | Phe | Val | Phe | Val | Cys 470 | Val | Phe | Gly | Thr | Ile 475 | Gly | Met | Phe | Leu | Gln 480 |
| Pro | Leu | Phe | Gln | Asn 485 | Tyr | Thr | Thr | Thr | Thr 490 | Phe | Leu | His | Ser | Asp 495 | His |
| Ser | Ala | Pro | Ser 500 | Ser | Lys | | | | | | | | | | |

( 2 ) INFORMATION FOR SEQ ID NO:5:

( i ) SEQUENCE CHARACTERISTICS:
( A ) LENGTH: 1915 base pairs (B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 87..1583

(xi) SEQUENCE DESCRIPTION: SEQ ID NO:5:

```
CCGGCGCTCA CTCGACCGCG CGGCTCACGG GTGCCCTGTG ACCCACAGC  GGAGCTCGCG      60
GCGGCTGCCA CCCGGCCCCG CCGGCCATGA GGCGCGCGCC TTCCCTGGTC CTTTTCTTCC     120
TGGTCGCCCT TTGCGGGCGC GGGAACTGCC GCGTGGCCAA TGCGGAGGAA AAGCTGATGG     180
ACGACCTTCT GAACAAAACC CGTTACAATA ACCTGATCCG CCCAGCCACC AGCTCCTCAC     240
AGCTCATCTC CATCAAGCTG CAGCTCTCCC TGGCCCAGCT TATCAGCGTG AATGAGCGAG     300
AGCAGATCAT GACCACCAAT GTCTGGCTGA ACAGGAATG  GACTGATTAC CGCCTGACCT     360
GGAACAGCTC CCGCTACGAG GGTGTGAACA TCCTGAGGAT CCCTGCAAAG CGCATCTGGT     420
TGCCTGACAT CGTGCTTTAC AACAACGCCG ACGGACCTA  TGAGGTGTCT GTCTACACCA     480
ACTTGATAGT CCGGTCCAAC GGCAGCGTCC TGTGGCTGCC CCCTGCCATC TACAAGAGCG     540
CCTGCAAGAT TGAGGTGAAG TACTTTCCCT TCGACCAGCA GAACTGCACC CTCAAGTTCC     600
GCTCCTGGAC CTATGACCAC ACGGAGATAG ACATGGTCCT CATGACGCCC ACAGCCAGCA     660
TGGATGACTT TACTCCCAGT GGTGAGTGGG ACATAGTGGC CCTCCAGGG  AGAAGGACAG     720
TGAACCCACA AGACCCCAGC TACGTGGACG TGACTTACGA CTTCATCATC AAGCGCAAGC     780
CTCTGTTCTA CACCATCAAC CTCATCATCC CTGCGTGCT  CACCACCTTG CTGGCCATCC     840
TCGTCTTCTA CCTGCCATCC GACTGCGGCG AGAAGATGAC ACTGTGCATC TCAGTGCTGC     900
TGGCACTGAC ATTCTTCCTG CTGCTCATCT CCAAGATCGT GCCACCCACC TCCCTCGATG     960
TGCCTCTCAT CGGCAAGTAC CTCATGTTCA CCATGGTGCT GGTCACCTTC TCCATCGYCA    1020
CCAGCGTCTG TGTGCTCAAT GTGCACCACC GCTCGCCCAG CACCCACACC ATGGCACCCT    1080
GGGTCAAGCG CTGCTTCCTG CACAAGCTGC CTACCTTCCT CTTCATGAAG CGCCCTGGCC    1140
CCGACAGCAG CCCGGCCAGA GCCTTCCCGC CAGCAAGTC  ATGCGTGACC AAGCCCGAGG    1200
CCACCGCCAC CTCCACCAGC CCCTCCAACT TCTATGGGAA CTCCATGTAC TTTGTGAACC    1260
CCGCCTCTGC AGCTTCCAAG TCTCCAGCCG GCTCTACCCC GGTGGCTATC CCCAGGGATT    1320
TCTGGCTGCG GYCCTCTGGG AGGTTCCGAC AGGATGTGCA GGAGGCATTA GAAGGTGTCA    1380
GCTTCATCGC CCAGCACATG AAGAATGDCG ATGAAGACCA GAGTGTCGCT GAGGACTGGA    1440
AGAACGTGGC TATGGTGGTG GACCGGCTGT TCCTGTGGGT GTTCATGTTT GTGTGCGTCC    1500
TGGGCTCTGT GGGGCTCTTC CTGCCGCCCC TCTTCCAGAC CCATGCAGCT TCTGAGGGGC    1560
CCTACGCTGC CCAGCGTGAC TGAGGGCCCC CTGGGTTGTG GGGTGAGAGG ATGTGAGTGG    1620
CCGGGTGGGC ACTTTGCTGC TTCTTTCTGG GTTGTGGCCG ATGAGGCCCT AAGTAAATAT    1680
GTGAGCATTG GCCATCAACC CCATCAAACC AGCCACAGCC GTGGAACAGG CAAGGATGGG    1740
GGCCTGGCCT GTCCTCTCTG AATGCTTGG  AGGGATCCCA GGAAGCCCCA GTAGGAGGGA    1800
GCTTCAGACA GTTCAATTCT GGCCTGTCTT CCTTCCCTGC ACCGGGCAAT GGGGATAAAG    1860
ATGACTTCGT AGCAGCACCT ACTATGCTTC AGGCATGGTG CCGGCCTGCC TCTCC         1915
```

(2) INFORMATION FOR SEQ ID NO:6:

(i) SEQUENCE CHARACTERISTICS:

( A ) LENGTH: 498 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:6:

| Met | Arg | Arg | Ala | Pro | Ser | Leu | Val | Leu | Phe | Phe | Leu | Val | Ala | Leu | Cys |
|---|---|---|---|---|---|---|---|---|---|---|---|---|---|---|---|
| 1 | | | | 5 | | | | | 10 | | | | | 15 | |
| Gly | Arg | Gly | Asn | Cys | Arg | Val | Ala | Asn | Ala | Glu | Glu | Lys | Leu | Met | Asp |
| | | | 20 | | | | | 25 | | | | | 30 | | |
| Asp | Leu | Leu | Asn | Lys | Thr | Arg | Tyr | Asn | Asn | Leu | Ile | Arg | Pro | Ala | Thr |
| | | | 35 | | | | 40 | | | | | 45 | | | |
| Ser | Ser | Ser | Gln | Leu | Ile | Ser | Ile | Lys | Leu | Gln | Leu | Ser | Leu | Ala | Gln |
| | 50 | | | | | 55 | | | | | 60 | | | | |
| Leu | Ile | Ser | Val | Asn | Glu | Arg | Glu | Gln | Ile | Met | Thr | Thr | Asn | Val | Trp |
| 65 | | | | | 70 | | | | | 75 | | | | | 80 |
| Leu | Lys | Gln | Glu | Trp | Thr | Asp | Tyr | Arg | Leu | Thr | Trp | Asn | Ser | Ser | Arg |
| | | | | 85 | | | | | 90 | | | | | 95 | |
| Tyr | Glu | Gly | Val | Asn | Ile | Leu | Arg | Ile | Pro | Ala | Lys | Arg | Ile | Trp | Leu |
| | | | | 100 | | | | | 105 | | | | | 110 | |
| Pro | Asp | Ile | Val | Leu | Tyr | Asn | Asn | Ala | Asp | Gly | Thr | Tyr | Glu | Val | Ser |
| | | | 115 | | | | | 120 | | | | | 125 | | |
| Val | Tyr | Thr | Asn | Leu | Ile | Val | Arg | Ser | Asn | Gly | Ser | Val | Leu | Trp | Leu |
| | 130 | | | | | 135 | | | | | 140 | | | | |
| Pro | Pro | Ala | Ile | Tyr | Lys | Ser | Ala | Cys | Lys | Ile | Glu | Val | Lys | Tyr | Phe |
| 145 | | | | | 150 | | | | | 155 | | | | | 160 |
| Pro | Phe | Asp | Gln | Gln | Asn | Cys | Thr | Leu | Lys | Phe | Arg | Ser | Trp | Thr | Tyr |
| | | | | 165 | | | | | 170 | | | | | 175 | |
| Asp | His | Thr | Glu | Ile | Asp | Met | Val | Leu | Met | Thr | Pro | Thr | Ala | Ser | Met |
| | | | 180 | | | | | 185 | | | | | 190 | | |
| Asp | Asp | Phe | Thr | Pro | Ser | Gly | Glu | Trp | Asp | Ile | Val | Ala | Leu | Pro | Gly |
| | | | 195 | | | | | 200 | | | | | 205 | | |
| Arg | Arg | Thr | Val | Asn | Pro | Gln | Asp | Pro | Ser | Tyr | Val | Asp | Val | Thr | Tyr |
| | 210 | | | | | 215 | | | | | 220 | | | | |
| Asp | Phe | Ile | Ile | Lys | Arg | Lys | Pro | Leu | Phe | Tyr | Thr | Ile | Asn | Leu | Ile |
| 225 | | | | | 230 | | | | | 235 | | | | | 240 |
| Ile | Pro | Cys | Val | Leu | Thr | Thr | Leu | Leu | Ala | Ile | Leu | Val | Phe | Tyr | Leu |
| | | | | 245 | | | | | 250 | | | | | 255 | |
| Pro | Ser | Asp | Cys | Gly | Glu | Lys | Met | Thr | Leu | Cys | Ile | Ser | Val | Leu | Leu |
| | | | | 260 | | | | | 265 | | | | | 270 | |
| Ala | Leu | Thr | Phe | Phe | Leu | Leu | Leu | Ile | Ser | Lys | Ile | Val | Pro | Pro | Thr |
| | | | 275 | | | | | 280 | | | | | 285 | | |
| Ser | Leu | Asp | Val | Pro | Leu | Ile | Gly | Lys | Tyr | Leu | Met | Phe | Thr | Met | Val |
| | 290 | | | | | 295 | | | | | 300 | | | | |
| Leu | Val | Thr | Phe | Ser | Ile | Xaa | Thr | Ser | Val | Cys | Val | Leu | Asn | Val | His |
| 305 | | | | | 310 | | | | | 315 | | | | | 320 |
| His | Arg | Ser | Pro | Ser | Thr | His | Thr | Met | Ala | Pro | Trp | Val | Lys | Arg | Cys |
| | | | | 325 | | | | | 330 | | | | | 335 | |
| Phe | Leu | His | Lys | Leu | Pro | Thr | Phe | Leu | Phe | Met | Lys | Arg | Pro | Gly | Pro |
| | | | 340 | | | | | 345 | | | | | 350 | | |
| Asp | Ser | Ser | Pro | Ala | Arg | Ala | Phe | Pro | Pro | Ser | Lys | Ser | Cys | Val | Thr |
| | | | 355 | | | | | 360 | | | | | 365 | | |
| Lys | Pro | Glu | Ala | Thr | Ala | Thr | Ser | Thr | Ser | Pro | Ser | Asn | Phe | Tyr | Gly |
| | 370 | | | | | 375 | | | | | 380 | | | | |

| | | | | | | | | | | | | | | | |
|---|---|---|---|---|---|---|---|---|---|---|---|---|---|---|---|
| Asn 385 | Ser | Met | Tyr | Phe | Val 390 | Asn | Pro | Ala | Ser | Ala 395 | Ala | Ser | Lys | Ser | Pro 400 |
| Ala | Gly | Ser | Thr | Pro 405 | Val | Ala | Ile | Pro | Arg 410 | Asp | Phe | Trp | Leu | Arg 415 | Xaa |
| Ser | Gly | Arg | Phe 420 | Arg | Gln | Asp | Val | Gln 425 | Glu | Ala | Leu | Glu | Gly 430 | Val | Ser |
| Phe | Ile | Ala 435 | Gln | His | Met | Lys | Asn 440 | Xaa | Asp | Glu | Asp | Gln 445 | Ser | Val | Ala |
| Glu | Asp 450 | Trp | Lys | Asn | Val | Ala 455 | Met | Val | Val | Asp | Arg 460 | Leu | Phe | Leu | Trp |
| Val 465 | Phe | Met | Phe | Val | Cys 470 | Val | Leu | Gly | Ser | Val 475 | Gly | Leu | Phe | Leu | Pro 480 |
| Pro | Leu | Phe | Gln | Thr 485 | His | Ala | Ala | Ser | Glu 490 | Gly | Pro | Tyr | Ala | Ala 495 | Gln |
| Arg | Asp | | | | | | | | | | | | | | |